US012187999B2

(12) United States Patent
Farmer et al.

(10) Patent No.: US 12,187,999 B2
(45) Date of Patent: Jan. 7, 2025

(54) REACTORS AND SUBMERGED FERMENTATION METHODS FOR PRODUCING MICROBE-BASED PRODUCTS

(71) Applicant: Locus Solutions IPCo, LLC, Solon, OH (US)

(72) Inventors: Sean Farmer, North Miami Beach, FL (US); Ken Alibek, Solon, OH (US); Tyler Dixon, Kent, OH (US); Nicholas Callow, Solon, OH (US); Kent Adams, Oro Valley, AZ (US); Karthik N. Karathur, Solon, OH (US)

(73) Assignee: Locus Solutions IPCo, LLC, Solon, OH (US)

( * ) Notice: Subject to any disclaimer, the term of this patent is extended or adjusted under 35 U.S.C. 154(b) by 1170 days.

(21) Appl. No.: 16/955,541

(22) PCT Filed: Dec. 22, 2018

(86) PCT No.: PCT/US2018/067409
§ 371 (c)(1),
(2) Date: Jun. 18, 2020

(87) PCT Pub. No.: WO2019/133555
PCT Pub. Date: Jul. 4, 2019

(65) Prior Publication Data
US 2020/0318051 A1 Oct. 8, 2020

Related U.S. Application Data

(60) Provisional application No. 62/611,300, filed on Dec. 28, 2017.

(51) Int. Cl.
C12M 1/06 (2006.01)
C12M 1/00 (2006.01)
C12M 1/02 (2006.01)
C12M 1/12 (2006.01)
C12N 1/16 (2006.01)

(52) U.S. Cl.
CPC ............ C12M 27/02 (2013.01); C12M 29/06 (2013.01); C12M 29/18 (2013.01); C12M 37/02 (2013.01); C12M 41/18 (2013.01); C12M 47/10 (2013.01); C12N 1/16 (2013.01)

(58) Field of Classification Search
None
See application file for complete search history.

(56) References Cited

U.S. PATENT DOCUMENTS

| 4,332,904 | A | 6/1982 | Kurane et al. |
| 6,620,614 | B1 * | 9/2003 | Luth ..................... C12M 23/24 |
| | | | 435/813 |
| 2004/0110273 | A1 | 6/2004 | Akers et al. |
| 2005/0266036 | A1 | 12/2005 | Awada et al. |
| 2005/0272146 | A1 | 12/2005 | Hodge et al. |
| 2008/0020437 | A1 | 1/2008 | Savarese |
| 2008/0138862 | A1 | 6/2008 | Felby et al. |
| 2009/0130757 | A1 | 5/2009 | Terentiev |
| 2009/0311772 | A1 | 12/2009 | Quinn |
| 2010/0015696 | A1 | 1/2010 | Claes et al. |
| 2010/0064746 | A1 | 3/2010 | Medoff |
| 2011/0044972 | A1 | 2/2011 | Fieldhouse et al. |
| 2011/0237531 | A1 | 9/2011 | Yanagisawa et al. |
| 2012/0021505 | A1 | 1/2012 | Kim et al. |
| 2012/0220464 | A1 | 8/2012 | Giessler-Blank et al. |
| 2012/0295332 | A1 | 11/2012 | Cheng |
| 2013/0260450 | A1 | 10/2013 | Fey et al. |
| 2013/0324406 | A1 | 12/2013 | Chisholm et al. |
| 2014/0024090 | A1 | 1/2014 | Doig et al. |
| 2015/0037302 | A1 | 2/2015 | Bralkowski et al. |
| 2015/0045290 | A1 * | 2/2015 | Coutte ..................... C12P 21/02 |
| | | | 530/321 |
| 2016/0083757 | A1 | 3/2016 | Fonseca et al. |
| 2017/0107477 | A1 | 4/2017 | Farmer et al. |
| 2017/0356022 | A1 * | 12/2017 | Khan ..................... C12M 47/10 |
| 2017/0362562 | A1 | 12/2017 | Nguyen et al. |

FOREIGN PATENT DOCUMENTS

| CN | 104450511 A | 3/2015 |
| CN | 105999763 A | 10/2016 |
| CN | 106135503 A | 11/2016 |
| EP | 3031895 A1 | 6/2016 |
| JP | 2016000017 A | 1/2016 |
| KR | 10-1114524 B1 | 2/2012 |
| KR | 10-1125189 B1 | 3/2012 |
| WO | 8103338 A1 | 11/1981 |
| WO | 9308263 A1 | 4/1993 |
| WO | 9525163 A1 | 9/1995 |
| WO | 03016461 A2 | 2/2003 |
| WO | 03093408 A1 | 11/2003 |
| WO | 2004020647 A1 | 3/2004 |
| WO | 2005117929 A1 | 12/2005 |
| WO | 2012088276 A2 | 6/2012 |
| WO | 2014159309 A1 | 10/2014 |

(Continued)

OTHER PUBLICATIONS

De Almeida, D., et al., "Biosurfactants: Promising Molecules for Petroleum Biotechnology Advances." Frontiers in Microbiology, 2016, 7(1718): 1-14.

(Continued)

Primary Examiner — Jana A Hines
Assistant Examiner — Khatol S Shahnan Shah
(74) Attorney, Agent, or Firm — SALIWANCHIK, LLOYD & EISENSCHENK

(57) ABSTRACT

Embodiments of the present invention provide novel, low-cost fermentation systems and methods of their use. More specifically, the present invention provides biological reactor systems for fermenting a wide variety of, for example, bio level 1 microorganisms with very high cell densities. The reactor systems can be used to grow yeast, fungi and bacteria, as well as growth by-products thereof. In specific embodiments, the reactor systems are used to produce yeast-based compositions. In certain specific embodiments, the reactor systems can be used for the production of *Starmerella bombicola* yeast compositions.

9 Claims, 4 Drawing Sheets

(56) References Cited

FOREIGN PATENT DOCUMENTS

| WO | 2015089183 A2 | 6/2015 |
|----|---------------|--------|
| WO | 2016092073 A1 | 6/2016 |
| WO | 2017220957 A1 | 12/2017 |
| WO | 2018049182 A2 | 3/2018 |
| WO | 2018129299 A1 | 7/2018 |

OTHER PUBLICATIONS

De Brito, D., Biosurfactants from renewable raw materials, Universidade do Minho Departamento de Engenharia Biologica, Nov. 2013, pp. 1-93.

De Oliveira, M., "Review: Sophorolipids A promising Biosurfactant and it's Applications." International Journal of Advanced Biotechnology and Research, 2015, 6(2): 161-174.

Elshafie, A., et al., "Sophorolipids Production by Candida Bombicola ATCC 22214 and its Potential Application in Microbial Enhanced Oil Recovery." Frontiers in Microbiology, 2015, 6(1324): 1-11.

Joaad, A., et al., "Effects of Different Environmental and Nutritional Factors on Biosurfactant Production from Candida Guilliermondii." Iraqi Journal of Science, 2015, 56(1B): 329-336.

Kurtzman, C., et al., "Production of Sophorolipid Biosurfactants by Multiple Species of the Starmerella (Candida) Bombicola Yeast Clade." FEMS Microbiology Letters, 2010, 311: 140-146.

Santos, D., et al., "Biosurfactants: Multifunctional Biomolecules of the 21st Century." International Journal of Molecular Sciences, 2016, 17(401): 1-31.

Sen, R., "Biosurfactants: Advances in Experimental Medicine and Biology." Landes Bioscience and Springer Science + Business Media, LLC, 2010, 672: 1-331.

Shah, M., et al., "Production of Sophorolipids by Starmerella Bombicola Yeast Using New Hydrophobic Substrates." Biochemical Engineering Journal, 2017, 127: 60-67.

Sharma, A., et al., "A Study on Biosurfactant Production in *Lactobacillus* and *Bacillus* SP." International Journal of Current Microbiology and Applied Sciences, 2014, 3(11): 723-733.

Takahashi, M., et al., "Production of Sophorolipid Glycolipid Biosurfactants from Sugarcane Molasses Using Starmerella Bombicola NBRC 10243." Journal of Oleo Science, 2011, 60(5): 267-273.

Zhang, Y., et al., "Semicontinuous Sophorolipid Fermentation Using a Novel Bioreactor with Dual Ventilation Pipes and Dual Sieve-Plates Coupled with a Novel Separation System." Microbial Biotechnology, 2018, 11(3): 455-464.

\* cited by examiner

REACTORS AND SUBMERGED FERMENTATION METHODS FOR PRODUCING MICROBE-BASED PRODUCTS

CROSS-REFERENCE TO A RELATED APPLICATION

This application is a National Stage Application of International Application No. PCT/US2018/067409, filed Dec. 22, 2018; which claims priority to U.S. Provisional Application No. 62/611,300, filed Dec. 28, 2017, both of which are incorporated herein by reference in its entirety.

BACKGROUND OF THE INVENTION

Cultivation of microorganisms such as bacteria, yeast and fungi is important for the production of a wide variety of useful bio-preparations. Microorganisms play crucial roles in, for example, oil and gas recovery, the food industry, pharmaceuticals, agriculture, mining, environmental remediation, and waste management.

There exists an enormous potential for the use of microbes in a broad range of industries. However, an important limiting factor in commercialization of microbe-based products has been the cost per propagule density, where it is particularly expensive and unfeasible to apply microbial products to large scale operations with sufficient inoculum to see the benefits.

Two principle forms of microbe cultivation exist: submerged cultivation and surface cultivation. Bacteria, yeasts and fungi can all be grown using either the surface or submerged cultivation methods. Both cultivation methods require a nutrient medium for the growth of the microorganisms. The nutrient medium, which can either be in a liquid or a solid form, typically includes a carbon source, a nitrogen source, salts and appropriate additional nutrients and microelements. The pH and oxygen levels are maintained at values suitable for a given microorganism.

Microbes and their growth by-products have the potential to play highly beneficial roles in, for example, the oil and agriculture industries, if only they could be made more readily available and, in the case of live microbes, in a more active and/or viable form.

Oil exists in small pores and narrow fissures within the body of reservoir rocks underneath the surface of the earth. Oil and natural gas are obtained by drilling into the earth's surface using what is generically referred to as a drilling rig. After the well is drilled, a production liner (or casing) is generally set and the well is then perforated (e.g., explosives are used to puncture the production liner at specific points in the oil bearing formation). Natural pressure of the reservoir causes the oil to flow up to the surface, thereby providing primary production; however as oil production progresses, the reservoir pressure is depleted to a point at which artificial lift or pumping is required to maintain an economical oil production rate.

A variety of different chemicals and equipment are utilized to prevent and remediate these obstacles, but they can be toxic and/or polluting. Thus, there is a need for improved products and methods that are more environmentally friendly, less toxic, and have enhanced effectiveness.

One such mechanism utilizes microbes and their by-products to enhance oil recovery, or microbial enhanced oil recovery (MEOR). Microbial by-products, which can include biosurfactants, biopolymers, acids, solvents, gases, and enzymes, for example, can modify the properties of the oil and the interactions between oil, water, and the porous media, alter the permeability of subterranean formations, and ultimately increase the mobility and recovery of oil.

Interest in microbial surfactants, in particular, has been steadily increasing in recent years due to their diversity, environmentally friendly nature, possibility of large-scale production, selectivity, performance under extreme conditions, and potential applications in environmental protection. Microbially produced surfactants, i.e., biosurfactants, reduce the interfacial tension between water and oil and, therefore, a lower hydrostatic pressure is required to move the liquid entrapped in the pores to overcome the capillary effect. Secondly, biosurfactants contribute to the formation of micelles providing a physical mechanism to mobilize oil in a moving aqueous phase. Furthermore, biosurfactants enhance the emulsification of hydrocarbons, have the potential to solubilize hydrocarbon contaminants and increase their availability for microbial degradation. These compounds can also be used in enhanced oil recovery.

In addition to their usefulness in the oil and gas industry, microbes and their metabolites are also a promising solution to the need for safe, efficacious, environmentally-friendly remedies to common obstacles in agricultural production. Farmers have relied heavily on the use of synthetic chemicals and chemical fertilizers to boost yields and protect crops against pathogens, pests, and disease; however, when overused or improperly applied, these substances can be air and water pollutants through runoff, leaching and evaporation. Even when properly used, the over-dependence and long-team use of certain chemical fertilizers and pesticides deleteriously alters soil ecosystems, reduces stress tolerance, increases pest resistance, and impedes plant and animal growth and vitality.

Mounting regulatory mandates governing the availability and use of chemicals, and consumer demands for residue free, sustainably-grown food produced with minimal harm to the environment, are impacting the industry and causing an evolution of thought regarding how to address the myriad of challenges. The demand for safer pesticides and alternate pest control strategies is increasing. While wholesale elimination of chemicals is not feasible at this time, farmers are increasingly embracing the use of biological measures as viable components of Integrated Nutrient Management and Integrated Pest Management programs.

For example, in recent years, biological control of nematodes has caught great interest. This method utilizes biological agents as pesticides, such as live microbes, bioproducts derived from these microbes, and combinations thereof. These biological pesticides have important advantages over other conventional pesticides, e.g., they are less harmful compared to the conventional chemical pesticides, they are more efficient and specific, and they often biodegrade quickly, leading to less environmental pollution.

While biological agents, such as microbes and, e.g., biosurfactants, have the potential to positively influence a variety of industrial operations, their use has been greatly limited by difficulties in production, transportation, administration, pricing and efficacy. For example, many microbes are difficult to grow and subsequently deploy, e.g., into an oil well or over an agricultural crop, in sufficient quantities to be useful. This problem is exacerbated by losses in viability and/or activity due to processing, formulating, storage and stabilizing prior to distribution. Furthermore, once applied, biological products may not thrive for any number of reasons including, for example, insufficient initial cell densities, the inability to compete effectively with the existing microflora at a particular location, and being introduced to formations, soil and/or other environmental conditions in which the microbe cannot flourish or even survive.

Microbe-based compositions could help resolve some of the aforementioned issues faced by the oil and gas industry, the agriculture industry, as well as many others. Thus, there is a need for more efficient cultivation methods for mass production of microorganisms and microbial metabolites for large-scale, industrial and commercial applications.

BRIEF SUMMARY OF THE INVENTION

The present invention provides materials, methods and systems for producing microbe-based compositions that can be used in the oil and gas industry, agriculture, health care and environmental cleanup, as well as for a variety of other applications. Specifically, the subject invention provides materials, methods and systems for efficient cultivation of microorganisms and production of microbial growth by-products.

Embodiments of the present invention provide unsophisticated, low-cost fermentation systems and methods of their use. More specifically, the present invention provides biological reactor systems for fermenting a wide variety of, for example, bio level 1 microorganisms with very high cell densities. The reactor systems can be used to grow yeast, fungi and bacteria, as well as growth by-products thereof. In specific embodiments, the reactor systems are used to produce yeast-based compositions, including, for example, compositions comprising *Starmerella bombicola*, *Wickerhamomyces anomalus*, and/or *Pseudozyma aphidis* yeast.

In certain specific embodiments, the reactor systems are used for the production of *Starmerella bombicola* yeast-based compositions.

In some embodiments, the yeast-based composition can be superior to, for example, purified microbial metabolites alone, due to, for example, the advantageous properties of yeast cells. These properties include high concentrations of mannoprotein as a part of yeast cell wall's outer surface (mannoprotein is a highly effective bioemulsifier) and the presence of the biopolymer beta-glucan (also an effective emulsifier) in yeast cell walls. Additionally, the yeast fermentation product further can comprise biosurfactants capable of reducing both surface and interfacial tension, enzymes, and other metabolites (e.g., lactic acid, ethyl acetate, ethanol, etc.), in the culture.

In some embodiments, the reactor systems can be used for the production of bacteria-based compositions, including, for example, compositions comprising *Bacillus* spp. (e.g., *B. subtilis, B. amyloliquefaciens, B. licheniformis*), and/or *Pseudomonas* spp. (e.g., *P. chlororaphis*).

In certain embodiments, the reactor systems can be used for the production of microbial metabolites, including, for example, enzymes, acids, solvents, alcohols, proteins, carbohydrates, vitamins, minerals, microelements, amino acids, bioemulsifiers, biopolymers, and biosurfactants. In one embodiment, the metabolite can be extracted from the fermentation broth and, optionally purified. In a specific embodiment, the systems are used to produce a biosurfactant, such as a glycolipid (e.g., sophorolipid, rhamnolipid, mannosylerythritol lipid, or trehalose lipid) or a lipopeptide (e.g., surfactin, iturin, fengycin, or lichenysin).

In preferred embodiments, the reactor systems of the subject invention comprise one high volume, vertical parallelepiped tank. Preferably, the tank is made of a metal or metal alloy, for example, stainless steel. The tank can have an opening at the top that can be sealed during operation and/or cleaning.

Depending upon the saturated oxygen requirements of the fermentation culture, the tank can be formatted as a stirred-tank reactor and/or an unstirred-tank reactor. In one embodiment, the tank is a modified stainless steel intermediate bulk container ("IBC").

Advantageously, the subject reactor systems can be scaled depending on the intended use. For example, the tank can range in volume from a few gallons to thousands of gallons. In some embodiments, the tank can hold about 1 to about 1,500 gallons. In some embodiments, a plurality of reactor systems can be set up inside an enclosure or housing facility to produce even greater total volumes of fermentation products.

In preferred embodiments, the reactor system utilizes a chaotic mixing scheme to circulate the culture and ensure highly efficient mass exchange. The chaotic mixing scheme uses an internal mixing apparatus as well as an external circulation system.

In one embodiment, the internal mixing apparatus comprises a mixing motor located at the top of the tank. The motor is rotatably attached to a metal shaft that extends into the tank and is fixed with an impeller to help propel tank liquid from the top of the tank to the bottom of the tank and to ensure efficient mixing and gas dispersion throughout the culture. In one embodiment, the metal shaft with the impeller rotates on a diagonal axis (e.g., an axis at 15 to 60° from vertical).

In one embodiment, the impeller is a standard four-blade Rushton impeller. In one embodiment, the impeller comprises an axial flow aeration turbine and/or a small marine propeller. In one embodiment, the impeller design comprises customized blade shapes to produce increased turbulence.

In one embodiment, the chaotic mixing scheme further utilizes an external circulation system. In preferred embodiments, the external circulation system doubles as a temperature control system. Advantageously, in certain embodiments, the external circulation system obviates the need for a double-walled tank or an external temperature control jacket.

In one embodiment, the external circulation system comprises two highly efficient external loops comprising inline heat exchangers. In one embodiment, the heat exchangers are shell-and-tube heat exchangers. Each loop is fitted with its own circulation pump.

The two pumps transport liquid from the bottom of the tank at, for example, 250 to 400 gallons per minute, through the heat exchangers, and back into the top of the tank. Advantageously, the high velocity at which the culture is pumped through the loops helps prevent cells from caking on the inner surfaces thereof.

The loops can be attached to a water source and, optionally, a chiller, whereby the water is pumped with a flow rate of about 10 to 15 gallons per minute around the culture passing inside the heat exchangers, thus increasing or decreasing temperature as desired. In one embodiment, the water controls the temperature of the culture without ever contacting the culture.

The reactor system can further comprise an aeration system capable of providing filtered air to the culture. The aeration system can, optionally, have an air filter for preventing contamination of the culture. The aeration system can function to keep the air level over the culture, the dissolved oxygen (DO), and the pressure inside the tank, at desired (e.g., constant) levels.

In certain embodiments, the unit can be equipped with a unique sparging system, through which the aeration system supplies air. Preferably, the sparging system comprises stainless steel injectors that produce microbubbles. In an exemplary embodiment, the spargers can comprise from 4 to 10 aerators, comprising stainless steel microporous pipes (e.g., having tens or hundreds of holes 1 micron or less in size), which are connected to an air supply. The unique microporous design allows for proper dispersal of oxygen throughout the culture, while preventing contaminating microbes from entering the culture through the air supply.

In some embodiments, the reactor system is controlled by a programmable logic controller (PLC). In certain embodiments, the PLC has a touch screen and/or an automated interface. The PLC can be used to start and stop the reactor system, and to monitor and adjust, for example, temperature, DO, and pH, throughout fermentation.

The reactor system can be equipped with probes for monitoring fermentation parameters, such as, e.g., pH, temperature and DO levels. The probes can be connected to a computer system, e.g., the PLC, which can automatically adjust fermentation parameters based on readings from the probes.

In certain embodiments, the DO is adjusted continuously as the microorganisms of the culture consume oxygen and reproduce. For example, the oxygen input can be increased steadily as the microorganisms grow, in order to keep the DO constant at about 30% (of saturation).

The reactor system can also be equipped with a system for running a steam sterilization cycle before and/or after running the reactor system. In certain embodiments, the steam sterilization system is automated.

The reactor system can comprise an off-gas system to release air. De-foaming measures can also be employed to suppress foam production, such as mechanical anti-foam apparatuses or chemical or biochemical additives.

In one embodiment, the subject invention provides methods of cultivating microorganisms without contamination using the subject reactor system. In certain embodiments, the methods of cultivation comprise adding a culture medium comprising water and nutrient components to the tank using, for example, a peristaltic pump; inoculating the reactor system with a viable microorganism; and optionally, adding an antimicrobial agent to the culture medium. The antimicrobial agent can be, for example, an antibiotic (when permissible based on e.g., location of use or product being produced) or a glycolipid (e.g., sophorolipids, rhamnolipids).

The method further comprises operating the system for an amount of time to achieve a desired cell concentration and/or a desired metabolite concentration within the culture. The microorganism and/or metabolite(s) can then be harvested for direct use, storage and/or processing.

In one embodiment, the subject invention further provides a composition comprising at least one type of microorganism and/or at least one microbial metabolite produced by the microorganism that has been grown using the subject reactor system. The microorganisms in the composition may be used in an active or inactive form. In some embodiments, the supernatant and growth by-products resulting from fermentation are separated from the microorganisms.

Advantageously, the method and equipment of the subject invention reduce the capital and labor costs of producing microorganisms and their metabolites on a large scale. Furthermore, the cultivation process of the subject invention reduces or eliminates the need to concentrate organisms after completing cultivation. The subject invention provides a cultivation method that not only substantially increases the yield of microbial products per unit of nutrient medium but simplifies production and facilitates portability.

Portability can result in significant cost savings as microbe-based compositions can be produced at, or near, the site of intended use. This means that the final composition can be manufactured on-site using locally-sourced materials if desired, thereby reducing shipping costs. Thus, the compositions can include viable microbes at the time of application, which can increase product effectiveness. Additionally, the compositions can be customized in real time to be ideal for conditions at a particular location.

Furthermore, in certain embodiments, the systems of the subject invention harness the power of naturally-occurring local microorganisms and their metabolic by-products. Use of local microbial populations can be advantageous in settings including, but not limited to, agriculture, environmental remediation (such as in the case of an oil spill), animal husbandry, aquaculture, forestry, pasture management, turf management, horticultural ornamental production, waste disposal and treatment, wastewater treatment, food production and procession, mining, oil recovery, and human health, including in remote locations.

DETAILED DESCRIPTION OF THE INVENTION

Figure 1:
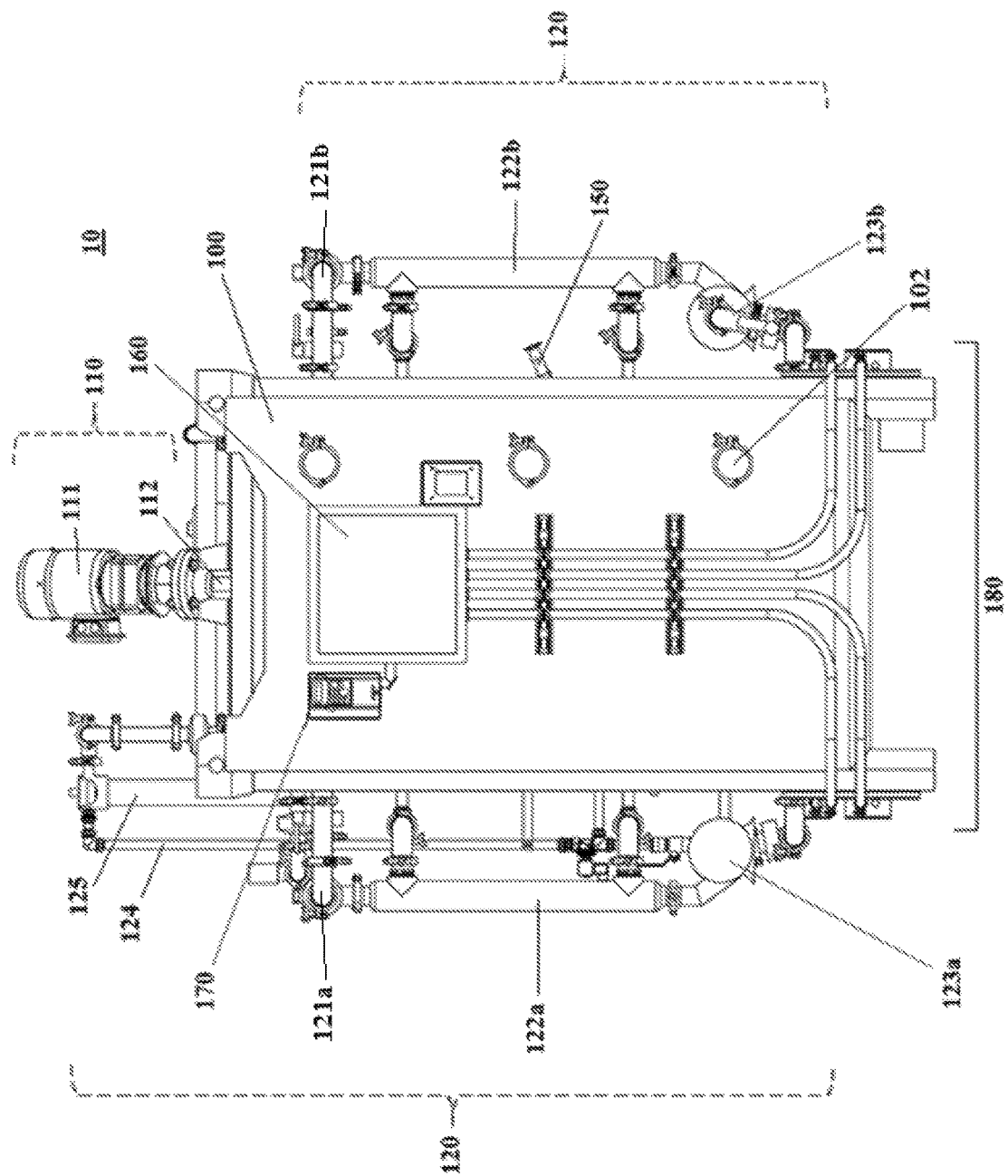
FIG. 1 shows a front view of a reactor system according to one embodiment of the invention.

The present invention provides materials, methods and systems for producing microbe-based compositions that can be used in the oil and gas industry, agriculture, health care and environmental cleanup, as well as for a variety of other applications. Specifically, the subject invention provides materials, methods and systems for efficient cultivation of microorganisms and production of microbial growth by-products.

Embodiments of the present invention provide unsophisticated, low-cost fermentation systems and methods of their use. More specifically, the present invention provides biological reactor systems for fermenting a wide variety of, for example, bio level 1 microorganisms with very high cell densities. The reactor systems can be used to grow yeast, fungi and bacteria, as well as growth by-products thereof. In specific embodiments, the reactor systems are used to produce yeast-based compositions, including, for example, compositions comprising *Starmerella bombicola*, *Wickerhamomyces anomalus*, and/or *Pseudozyma aphidis* yeast.

In certain specific embodiments, the reactor systems are used for the production of *Starmerella bombicola* yeast-based compositions.

In some embodiments, the yeast-based composition can be superior to, for example, purified microbial metabolites alone, due to, for example, the advantageous properties of yeast cells. These properties include high concentrations of mannoprotein as a part of yeast cell wall's outer surface (mannoprotein is a highly effective bioemulsifier) and the presence of the biopolymer beta-glucan (also an effective emulsifier) in yeast cell walls. Additionally, the yeast fermentation product further can comprise biosurfactants capable of reducing both surface and interfacial tension, enzymes, and other metabolites (e.g., lactic acid, ethyl acetate, ethanol, etc.), in the culture.

In some embodiments, the reactor systems can be used for the production of bacteria-based compositions, including, for example, compositions comprising *Bacillus* spp. (e.g., *B. subtilis, B. amyloliquefaciens, B. licheniformis*), and/or *Pseudomonas* spp. (e.g., *P. chlororaphis*).

In certain embodiments, the reactor systems can be used for the production of microbial metabolites, including, for example, enzymes, acids, solvents, alcohols, proteins, carbohydrates, vitamins, minerals, microelements, amino acids, bioemulsifiers, biopolymers, and biosurfactants. In one embodiment, the metabolite can be extracted from the fermentation broth and, optionally purified. In a specific embodiment, the systems are used to produce a biosurfactant, such as a glycolipid (e.g., sophorolipid, rhamnolipid, mannosylerythritol lipid, or trehalose lipid) or a lipopeptide (e.g., surfactin, iturin, fengycin, or lichenysin).

Selected Definitions

As used herein, reference to a "microbe-based composition" means a composition that comprises components that were produced as the result of the growth of microorganisms or other cell cultures. Thus, the microbe-based composition may comprise the microbes themselves and/or by-products of microbial growth. The microbes may be in a vegetative state, in spore form, in mycelial form, in any other form of propagule, or a mixture of these. The microbes may be planktonic or in a biofilm form, or a mixture of both. The by-products of growth may be, for example, metabolites, cell membrane components, expressed proteins, and/or other cellular components. The microbes may be intact or lysed. In some embodiments, the microbes are present, with broth in which they were grown, in the microbe-based composition. The cells may be present at, for example, a concentration of $1\times10^4$, $1\times10^5$, $1\times10^6$, $1\times10^7$, $1\times10^8$, $1\times10^9$, $1\times10^{10}$, $1\times10^{11}$, $1\times10^{12}$ or $1\times10^{13}$ or more cells per milliliter of the composition. In some embodiments, the microbe-based composition comprises microbial metabolites that have been extracted and/or separated from the fermentation broth and/or microbes.

The subject invention further provides "microbe-based products," which are products that are to be applied in practice to achieve a desired result. The microbe-based product can be simply the microbe-based composition harvested from the microbe cultivation process. Alternatively, the microbe-based product may comprise further ingredients that have been added. These additional ingredients can include, for example, stabilizers, buffers, appropriate carriers, such as water, salt solutions, or any other appropriate carrier, added nutrients to support further microbial growth, non-nutrient growth enhancers, such as plant hormones, and/or agents that facilitate tracking of the microbes and/or the composition in the environment to which it is applied. The microbe-based product may also comprise mixtures of microbe-based compositions. The microbe-based product may also comprise one or more components of a microbe-based composition that have been processed in some way such as, but not limited to, filtering, centrifugation, lysing, drying, purification and the like.

As used herein, "harvested" refers to removing some or all of a microbe-based composition from a growth vessel.

As used herein, a "biofilm" is a complex aggregate of microorganisms, such as bacteria, wherein the cells adhere to each other. The cells in biofilms are physiologically distinct from planktonic cells of the same organism, which are single cells that can float or swim in liquid medium.

As used herein, "control" of a microorganism refers to the act of killing, disabling, eliminating, immobilizing or reducing the population numbers of the microorganism, or otherwise rendering the microorganism substantially incapable of causing harm.

As used herein, an "isolated" or "purified" nucleic acid molecule, polynucleotide, polypeptide, protein, organic compound such as a small molecule (e.g., those described below), or other compound is substantially free of other compounds, such as cellular material, with which it is associated in nature. For example, a purified or isolated polynucleotide (ribonucleic acid (RNA) or deoxyribonucleic acid (DNA)) is free of the genes or sequences that flank it in its naturally-occurring state. A purified or isolated polypeptide is free of the amino acids or sequences that flank it in its naturally-occurring state. A purified or isolated microbial strain is removed from the environment in which it exists in nature. Thus, the isolated strain may exist as, for example, a biologically pure culture, or as spores (or other forms of the strain) in association with a carrier.

In certain embodiments, purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis.

A "metabolite" refers to any substance produced by metabolism (e.g., a growth by-product) or a substance necessary for taking part in a particular metabolic process. A metabolite can be an organic compound that is a starting material (e.g., glucose), an intermediate (e.g., acetyl-CoA) in, or an end product (e.g., n-butanol) of metabolism. Examples of metabolites can include, but are not limited to, enzymes, toxins, acids, solvents, alcohols, proteins, carbohydrates, vitamins, minerals, microelements, amino acids, polymers, and biosurfactants.

As used herein, "surfactant" refers to a surface-active compound that lowers the surface tension (or interfacial tension) between two liquids or between a liquid and a solid. Surfactants act as, e.g., detergents, wetting agents, emulsifiers, foaming agents, and dispersants. A "biosurfactant" is a surfactant produced by a living organism.

As used herein, "intermediate bulk container," "IBC" or "pallet tank" refers to a reusable industrial container designed for transporting and storing bulk substances, including, e.g., chemicals (including hazardous materials), food ingredients (e.g., syrups, liquids, granulated and powdered ingredients), solvents, detergents, adhesives, water and pharmaceuticals. Typically, IBCs are stackable, mounted on a pallet, and/or are otherwise designed to be moved using a forklift or a pallet jack. Thus, IBCs are designed to enable portability.

The transitional term "comprising," which is synonymous with "including," or "containing," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Unless specifically stated or obvious from context, as used herein, the term "or" is understood to be inclusive. Unless specifically stated or obvious from context, as used herein, the terms "a," "an" and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

Reactor System Design and Operation

Figure 2:
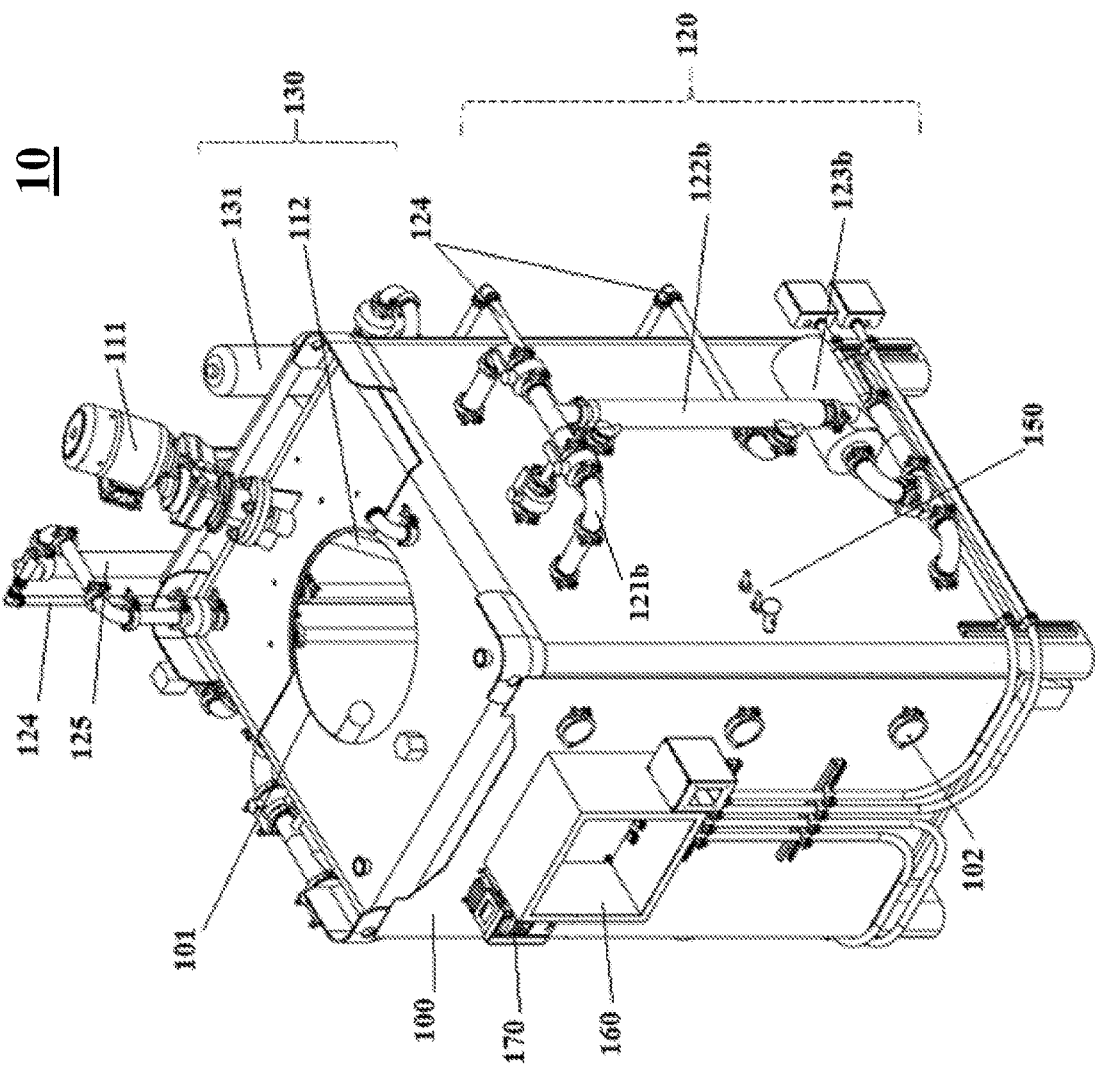
FIG. 2 shows an isometric view of a reactor system according to one embodiment of the subject invention. The front, right side, and top of the system are shown.
Figure 3:
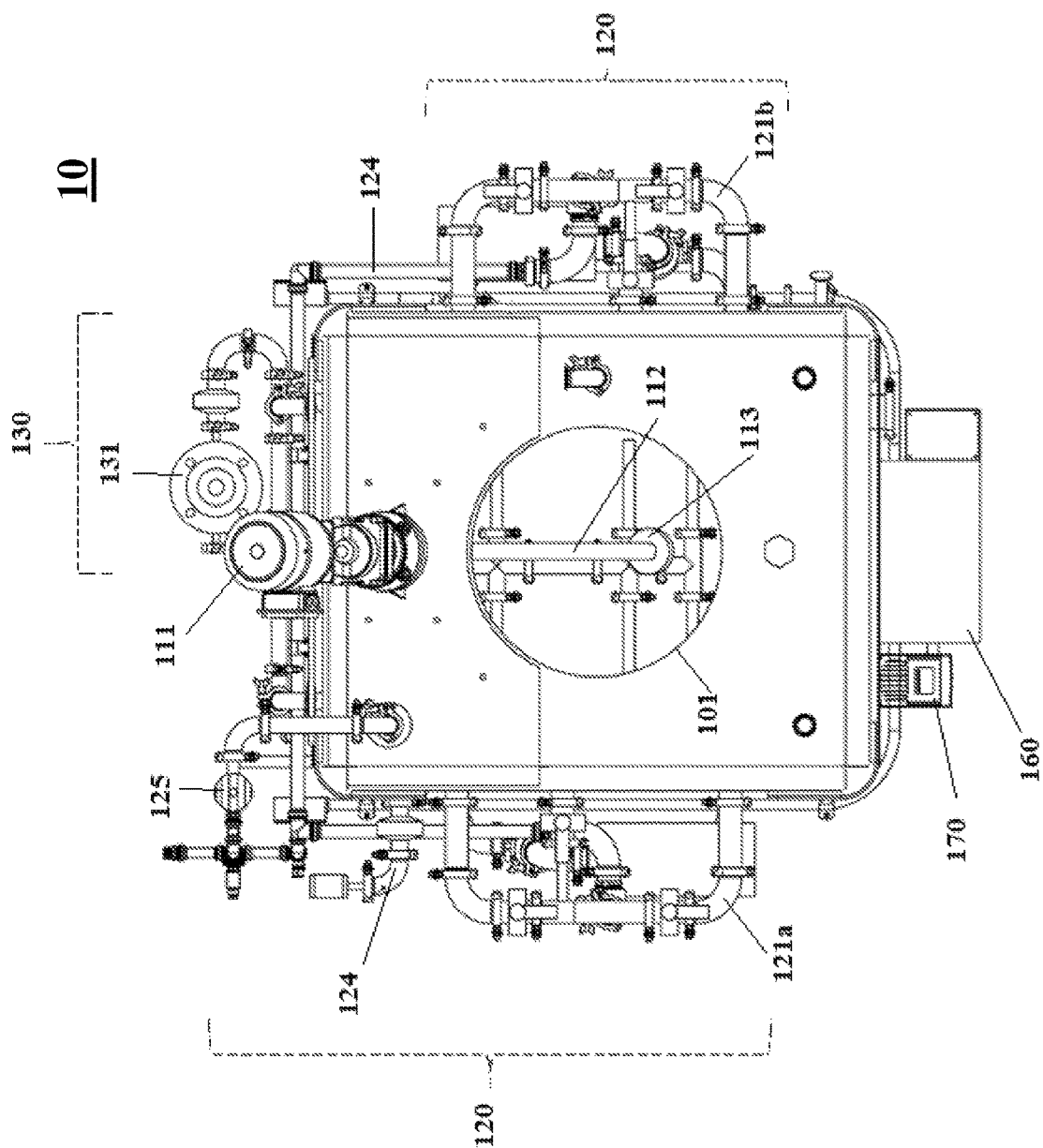
FIG. 3 shows a top-down view of a reactor system, with the opening at the top in an unsealed state, according to one embodiment of the subject invention.
Figure 4:
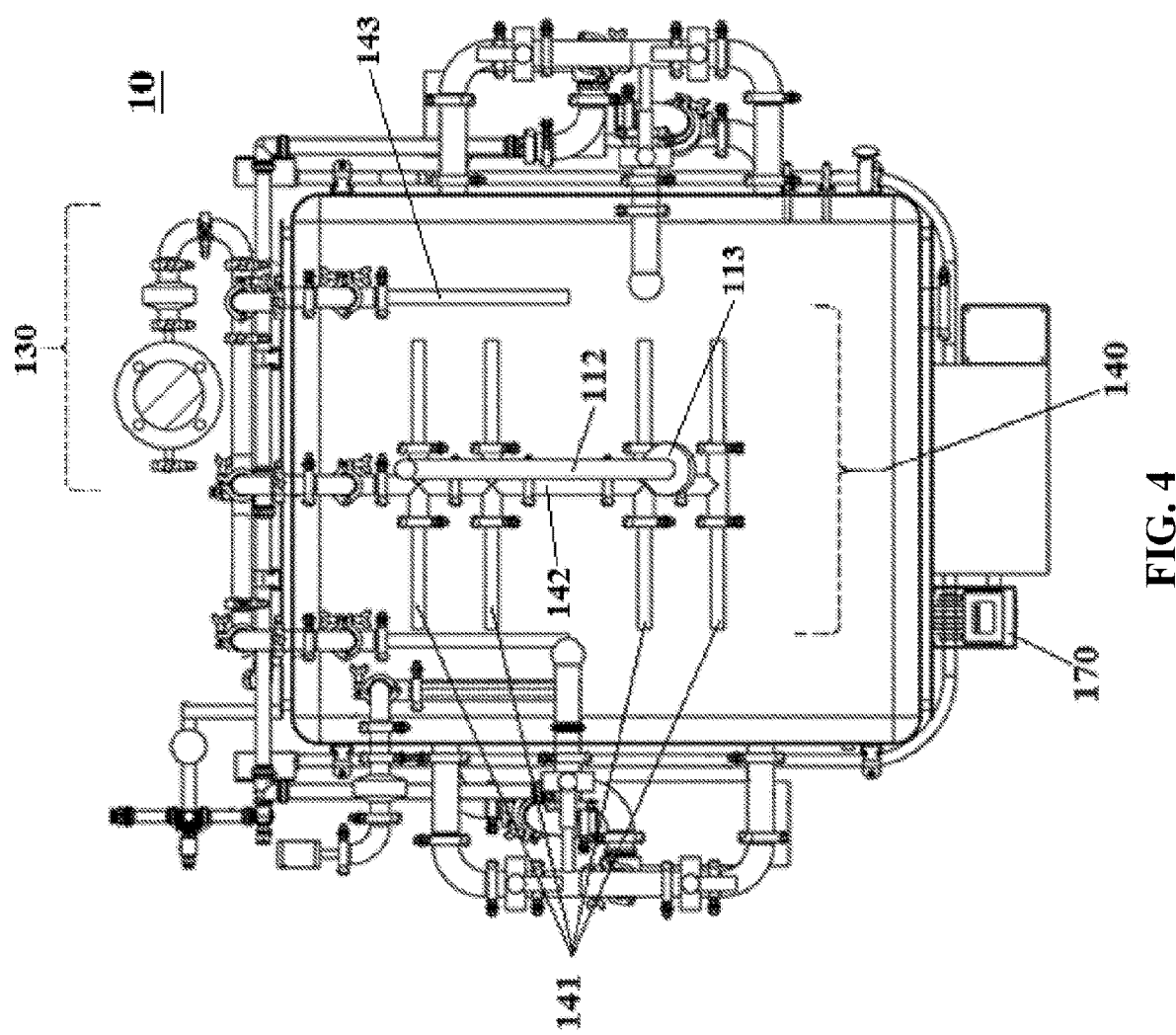
FIG. 4 shows a top-down view of the inside of a reactor system according to one embodiment of the subject invention.

Referring to FIGS. 1-4, embodiments of the reactor system of the subject invention can comprise the following components. In one embodiment, the reactor system 10 of the subject invention comprises one high volume, vertical parallelepiped tank 100. Depending upon the saturated oxygen requirements of the fermentation culture, the tank 100 can be formatted as a stirred-tank reactor and/or an unstirred-tank reactor. In one embodiment, the reactor system 10 is used as a batch reactor (as opposed to a continuous reactor).

The tank 100 according to the subject invention can be any fermenter or cultivation reactor for industrial use. The tank 100 may be made of, for example, glass, polymers, metals, metal alloys, and/or combinations thereof.

Preferably, the tank 100 is made of metal, for example, stainless steel. In one embodiment, the tank 100 is a stainless steel intermediate bulk container ("IBC") that has been modified for use as a fermentation reactor. The tank 100 can have a sealable opening 101 located, for example, at the top. The tank 100 can also have one or more sight glasses 102 for visual monitoring of the culture inside the tank 100.

Advantageously, the reactor system 10 can be scaled depending on the intended use. For example, the tank 100 can range in volume from a few gallons to thousands of gallons. In one embodiment, the ratio of tank 100 width to height is 1:2 to 1:5.

In some embodiments, the tank 100 can hold about 1 to about 1,500 gallons. In some embodiments, the tank 100 can hold about 5 liters to 5,000 liters or more. Typically, the tank 100 will be from 10 to 4,000 liters, and preferably from 100 to 2,500 liters.

In one exemplary embodiment, the tank 100 has a volume of 550 gallons (about 2,082 liters) and measures 5 by 5 feet in length and width, and about 6 feet in height.

In some embodiments, a plurality of individual reactor systems 10 can be set up inside an enclosure or housing facility to produce even greater total volumes of fermentation products.

In preferred embodiments, the reactor system 10 utilizes a chaotic mixing scheme 110 and 120 to circulate the culture. The chaotic mixing scheme 110 and 120 uses an internal mixing apparatus 110 as well as an external circulation system 120.

In one embodiment, the internal mixing apparatus 110 comprises a mixing motor 111 located at the top of the tank 100. In one embodiment, the mixing motor 111 rotates on a diagonal axis (e.g., an axis at 15 to 60° from vertical). The motor 111 is rotatably attached to a metal shaft 112 that extends into the tank 100 and is fixed with an impeller 113 to help propel liquid from the top of the tank 100 to the bottom of the tank 100 and to ensure efficient mixing and gas dispersion throughout the culture, as well as efficient mass exchange. In some embodiments, the shaft 112 is fixed with two or more impellers (not shown).

In one embodiment, the impeller 113 is a standard four-blade Rushton impeller. In one embodiment, the impeller 113 comprises an axial flow aeration turbine (not shown) and/or a small marine propeller (not shown). In one embodiment, the impeller 113 design comprises customized blade shapes to produce increased turbulence.

In one embodiment, the chaotic mixing scheme 110 and 120 further utilizes an external circulation system 120. In preferred embodiments, the external circulation system 120 doubles as a temperature control system. Advantageously, the external circulation system 120 obviates the need for a double-walled tank 100, or an external temperature control jacket.

In one embodiment, the external circulation system 120 comprises a first and a second highly efficient external loop 121a, 121b comprising a first and a second inline 300K to 360K heat exchanger 122a, 122b. Either or both of the loops 121a, 121b can be located on either side of the tank 100 and/or on the back of the tank 100.

In one embodiment, the heat exchangers 122a, 122b are shell-and-tube heat exchangers. Each loop 121a, 121b is fitted with its own 1-2 horsepower circulation pump 123a, 123b.

The two pumps 123a, 123b transport liquid from the bottom of the tank 100 at, for example, 250 to 400 gallons per minute, through the first and second heat exchangers 122a, 122b, and back into the tank 100 at the top. Advantageously, the velocity at which the culture is pumped through the two loops 121a, 121b helps prevent cells from caking on the inner surfaces thereof.

The first and second loops 121a, 121b can be attached to a water source 124, and optionally, a chiller, whereby the water is pumped with a flow rate of about 10 to 15 gallons per minute around the culture passing inside the heat exchangers 122a, 122b, thus increasing or decreasing temperature as desired. In some embodiments, the water is filtered through a water filter 125.

The heat exchangers 122a, 122b can utilize an electric heater (not shown); however, for larger applications where heat is required, steam or hydrocarbon fuel can be utilized to generate heat. For example, steam input and/or a steam source (not shown) can be connected to the heat exchangers 122a, 122b.

The heat exchangers 122a, 122b provide a closed system where the cooling water or steam used for temperature control do not contact the culture. Advantageously, the external circulation system 120 can also be used to clean the reactor system 10 in between cycles, wherein steam and/or hot water is circulated through the tank 10 and the external loops 121a, 121b for a time sufficient to remove cell matter and any other contaminants.

In one embodiment, the reactor system 10 may be adapted to ensure maintenance of an appropriate fermentation temperature, particularly if the reactor system 10 is being operated outdoors. In preferred embodiments, however, such adaptations are not necessary due to the use of the external circulation system 120. For example, the outside of the reactor system 10 can be reflective to avoid raising the system 10 temperature during the day if being operated outdoors. The reactor system 10 can also be insulated so the fermentation process can remain at appropriate temperatures in low temperature environments. Any of the insulating materials known in the art can be applied including fiberglass, silica aerogel, ceramic fiber insulation, etc. The insulation (not shown) can surround any and/or all of the components of the system 10.

The reactor system 10 can further comprise an aeration system 130. The aeration system 130 can, optionally, have an air filter 131 for preventing contamination of the culture. The aeration system 130 can function to keep the air level over the culture, the DO, and the pressure inside the tank 100, at desired (e.g., constant) levels.

In certain embodiments, the reactor system 10 can be equipped with a unique sparging system 140, through which the aeration system 130 supplies air. In some embodiments, the sparging system 140 is fixed at the bottom of the tank 100.

Preferably, the sparging system 140 comprises multiple aerators 141 that produce microbubbles of air. In an exemplary embodiment, the sparging system 140 comprises from 4 to 10 aerators 141, comprising stainless steel microporous pipes connected perpendicularly to a central air supply pipe 142. The microporous pipes comprise a plurality (e.g., tens to hundreds) of holes (not shown), through which air is injected into the culture in the form of microbubbles.

In preferred embodiments, the holes in the microporous pipes of the aerators 141 are 1 micron in diameter or less, preferably about 0.01 to 0.5 micron, more preferably, about 0.1 to 0.2 micron. The unique microporous design allows for dispersal of oxygen throughout the culture. Furthermore, injection of air through submicron-sized holes prevents contaminating microbes from entering the culture through the aeration system 130 and air supply 142.

In some embodiments, the sparging system 140 comprises one or more additional aerators 143. The additional aerators 143 can be fixed to the tank 100 bottom or can protrude into the tank 100 from a point between the bottom and the top of the tank 100, for example, at the midpoint of the height of the tank 100.

In one embodiment, the impeller 113 helps keep the microbubbles from coalescing into larger-sized bubbles.

The reactor system 10 can be equipped with a system (not shown) for running a steam sterilization cycle before and/or after running the reactor system 10. In certain embodiments, the steam sterilization system is automated.

The reactor system 10 can comprise an off-gas system to release air (not shown). De-foaming measures can also be employed to suppress foam production, such as mechanical anti-foam apparatuses or addition of chemical or biochemical anti-foam additives.

In some embodiments, the reactor system 10 is controlled by a programmable logic controller (PLC) 170. In certain embodiments, the PLC 170 has a touch screen and/or an automated interface. The PLC 170 can be used to start and stop the reactor system, and to monitor and implement adjustments to, for example, temperature, DO, and pH, throughout fermentation. Desired measurements can be programmed into the computer 170 prior to the reactor system 10 being delivered to a site, or on-site prior to operation.

In one embodiment, the reactor system 10 has functional controls/sensors/probes 150 or may be capable of being connected to functional controls/sensors/probes for measuring cultivation parameters either automatically or manually. These parameters can include, for example, pH, DO, pressure, temperature, agitator shaft power, humidity, viscosity, microbial density and/or metabolite concentration.

The probes 150 can be connected to a computer system, e.g., the PLC 170, which utilizes an electronic panel 160 to implement adjustments to fermentation parameters based on readings from the probes 150. Adjustments can be made automatically or can be directed manually by a user.

The pH can be set to a specific number by a user or the computer 170 can be pre-programmed to direct changes in the pH according to probe 150 readings throughout the fermentation process. If the pH adjustment is to be done manually, pH measurement tools known in the art can be included with the system for manual testing.

The temperature can be set to a specific measurement by a user or the computer 170 can be pre-programmed to direct changes in the temperature according to probe 150 readings throughout the fermentation process. In certain embodiments, the temperature probe 150 is a thermometer. The temperature measurements can be used to automatically or manually control the temperature control systems that are discussed above.

In certain embodiments, the DO is monitored and adjusted continuously as the microorganisms of the culture consume oxygen and reproduce. For example, in response to DO readings from the probes 150, the computer 170 can direct the aeration system 130 to keep the DO constant at about 30% (of saturation). In one embodiment, this can be achieved by cascade, where the amount of oxygen input is increased steadily as the microorganisms grow and consume greater amounts thereof.

In addition to monitoring and controlling temperature and pH, each reactor system 10 may also have the capability for monitoring and controlling, for example, agitation, foaming, purity of microbial cultures, production of desired metabolites and the like. The reactor systems 10 can further be adapted for remote monitoring of these parameters (not shown), for example with a tablet, smart phone, or other mobile computing device capable of sending and receiving data wirelessly.

In a further embodiment, the tanks 10 may also be able to monitor the growth of microorganisms inside the vessel (e.g., measurement of cell number and growth phases). Alternatively, a daily sample may be taken from the vessel and subjected to enumeration by techniques known in the art, such as dilution plating technique. Dilution plating is a simple technique used to estimate the number of bacteria in a sample. The technique can also provide an index by which different environments or treatments can be compared.

In one embodiment, the reactor system 10 is a mobile or portable bioreactor that may be provided for on-site production of a microbiological product including a suitable amount of a desired strain of microorganism. Because the microbiological product is generated on-site of the application, without resort to the bacterial stabilization, preservation, storage and transportation processes of conventional production, a much higher density of live microorganisms may be generated, thereby requiring a much smaller volume of the microorganism composition for use in the on-site application. This allows for a scaled-down bioreactor (e.g., smaller fermentation tanks, smaller supplies of starter material, nutrients, pH control agents, and de-foaming agent, etc.), which facilitates the mobility and portability of the system.

The reactor system 10 can include a frame or a stand 180 for supporting the apparatus 10 components. The system 10 can include wheels (not shown) for moving the apparatus 10, as well as handles (not shown) for steering, pushing and pulling when maneuvering the apparatus 10. Furthermore, the system 10 can comprise forklift pockets (not shown) for efficient transport using a forklift.

The reactor system 10 can be suitable for transport on a pickup truck, a flatbed trailer, or a semi-trailer, or can even be configured onto the back of a flatbed truck, truck trailer and/or semi-trailer.

Microorganisms

The microbes and their growth products produced according to the subject invention can serve as microbial factories to produce a vast array of useful products, including, for example, pure or crude-form biosurfactants, ethanol, biopesticides, nutritional compounds, therapeutic proteins such as insulin, compounds useful as vaccines, enzymes, and biopolymers.

The microorganisms can be, for example, bacteria, yeast and/or fungi. These microorganisms may be natural, or genetically modified microorganisms. For example, the microorganisms may be transformed with specific genes to exhibit specific characteristics. The microorganisms may also be mutants of a desired strain. As used herein, "mutant" means a strain, genetic variant or subtype of a reference microorganism, wherein the mutant has one or more genetic variations (e.g., a point mutation, missense mutation, nonsense mutation, deletion, duplication, frameshift mutation or repeat expansion) as compared to the reference microorganism. Procedures for making mutants are well known in the microbiological art. For example, UV mutagenesis and nitrosoguanidine are used extensively toward this end.

In one embodiment, the microorganism is a yeast or fungus. Yeast and fungus species suitable for use according to the current invention, include *Acaulospora, Aspergillus, Aureobasidium* (e.g., *A. pullulans*), *Blakeslea, Candida* (e.g., *C. albicans, C. apicola, C. batistae, C. bombicola, C. floricola, C. kuoi, C. riodocensis, C. stellate*), *Debaryomyces* (e.g., *D. hansenii*), *Entomophthora, Hanseniaspora* (e.g., *H. uvarum*), *Hansenula, Issatchenkia, Kluyveromyces, Mortierella, Mucor* (e.g., *M. piriformis*), *Penicillium, Phythium, Phycomyces, Pichia* (e.g., *P. anomala, P. guielliermondii, P. occidentalis, P. kudriavzevii*), *Pseudozyma* (e.g., *P. aphidis*), *Rhizopus, Rhodotorula* (e.g., *R. bogoriensis*); *Saccharomyces* (*S. cerevisiae, S. boulardii sequela, S. torula*), *Starmerella* (e.g., *S. bombicola*), *Torulopsis, Thraustochytrium, Trichoderma* (e.g., *T. reesei, T. harzianum, T. virens*), *Ustilago* (e.g., *U. maydis*), *Wickerhamiella* (e.g., *W. domericqiae*), *Wickerhamomyces* (e.g., *W. anomalus*), *Williopsis, Zygosaccharomyces*.

In one embodiment, the microorganism is a yeast known as a "killer yeast." As used herein, "killer yeast" means a strain of yeast characterized by its secretion of toxic proteins or glycoproteins, to which the strain itself is immune. The exotoxins secreted by killer yeasts are capable of killing other strains of yeast, fungi, or bacteria. Killer yeasts can include, but are not limited to species of, for example, *Candida* (e.g., *C. nodaensis*), *Cryptococcus, Debaryomyces* (e.g., *D. hansenii*), *Hanseniaspora*, (e.g., *H. uvarum*), *Hansenula, Kluyveromyces* (e.g., *K. phaffii*), *Pichia* (e.g., *P. anomala, P. guielliermondii, P. occidentalis, P. kudriavzevii*), *Saccharomyces* (e.g., *S. cerevisiae*), *Torulopsis, Ustilago* (e.g., *U. maydis*), *Wickerhamomyces* (e.g., *W. anomalus*), *Williopsis* (e.g., *W. mrakii*), *Zygosaccharomyces* (e.g., *Z. bailii*), and others.

In one embodiment, the microorganism is a biosurfactant-producing yeast. For example, *Starmerella bombicola* and *Wickerhamomyces anomalus* are capable of producing glycolipids. *Pseudozyma aphidis*, on the other hand, is capable of producing mannosylerythritol lipids.

The system can also be used to produce one or more strains of yeast capable of enhancing oil recovery and performing paraffin degradation, e.g., *Starmerella (Candida) bombicola, Candida apicola, Candida batistae, Candida floricola, Candida riodocensis, Candida stellate, Candida kuoi, Candida* sp. NRRL Y-27208, *Rhodotorula bogoriensis* sp., *Wickerhamiella domericqiae*, as well as any other glycolipid-producing strains of the *Starmerella* clade.

In certain embodiments, the microorganisms are bacteria, including Gram-positive and Gram-negative bacteria. The bacteria may be, for example, *Agrobacterium* (e.g., *A. radiobacter*), *Arthrobacter* (e.g., *A. radiobacter*), *Azomonas* spp., *Azotobacter* (*A. vinelandii, A. chroococcum*), *Azospirillum* (e.g., *A. brasiliensis*), *Bacillus* (e.g., *B. amyloliquifaciens, B. firmus, B. laterosporus, B. licheniformis, B. megaterium, Bacillus mucilaginosus, B. subtilis*), *Beijerinckia* spp., *Bradyrhizobium* (e.g., *B. japanicum*, and *B. parasponia*), *Clavibacter* (e.g., *C. xyli* subsp. *xyli* and *C. xyli* subsp. *cynodontis*), *Clostridium* (*C. butyricum, C. lyrobutyricum, C. acetobutyricum, Clostridium* NIPER 7, and *C. beijerinckii*), *Cyanobacteria* spp., *Derxia* spp., *Erwinia* (e.g., *E. carotovora*), *Escherichia coli, Frateuria* (e.g., *F. aurantia*), *Klebsiella* spp., *Microbacterium* (e.g., *M. laevaniformans*), *Pantoea* (e.g., *P. agglomerans*), *Nocardia* spp., *Pantoea* (e.g., *P. agglomerans*), *Pseudomonas* (e.g., *P. aeruginosa, P. chlororaphis* subsp. *aureofaciens* (*Kluyver*), *P. putida*), *Ralslonia* (e.g., *R. eulropha*), *Rhizobium* (e.g., *R. japonicum, Sinorhizobium meliloti, Sinorhizobium fredii, R. leguminosarum biovar trifolii*, and *R. etli*), *Rhodospirillum* (e.g., *R. rubrum*), *Sphingomonas* (e.g., *S. paucimobilis*), *Streptomyces* (e.g., *S. griseochromogenes, S. qriseus, S. cacaoi, S. aureus*, and *S. kasugaenis*), *Streptoverticillium* (e.g., *S. rimofaciens*), and/or *Xanthomonas* (e.g., *X. campestris*).

In one embodiment, the microorganism is a strain of *B. subtilis*, such as, for example, *B. subtilis* var. *locuses* B1 or B2, which are effective producers of, for example, surfactin and other lipopeptide biosurfactants. This specification incorporates by reference International Publication No. WO 2017/044953 A1 to the extent it is consistent with the teachings disclosed herein. In another embodiment, the microorganism is a strain of *Bacillus licheniformis*, which is an effective producer of lipopeptide biosurfactants, such as lichenysin, as well as biopolymers, such as levan.

In one embodiment, the microbe is a non-pathogenic strain of *Pseudomonas*, such as *P. chlororaphis*.

Other microbial strains including strains capable of accumulating significant amounts of, for example, glycolipids, lipopeptides, mannoprotein, beta-glucan and other metabolites that have useful industrial properties (e.g., bio-emulsifying properties, surface/interfacial tension-reducing properties), can be used in accordance with the subject invention.

In one embodiment, a single type of microbe is grown a reactor system. In alternative embodiments, multiple microbes, which can be grown together without deleterious effects on growth or the resulting product, can be grown in a single reactor system. There may be, for example, 2 to 3 or more different microbes grown in a single reactor at the same time. In some embodiments, the more than one microbes grow symbiotically in the reactor.

Microbial Growth By-Products

The methods and systems of the subject invention can be used to produce useful microbial growth by-products such as, for example, biosurfactants, enzymes, acids, biopolymers, solvents, and/or other microbial metabolites. A microorganism is cultivated under conditions favorable for production of the metabolite, the metabolite is extracted from the product of culture and, optionally, purified and/or concentrated.

In specific embodiments, the growth by-product is a biosurfactant. In preferred embodiments, the biosurfactants is a glycolipid or a lipopeptide.

Biosurfactants are a structurally diverse group of surface-active substances produced by microorganisms. Biosurfactants are biodegradable and can be easily and cheaply produced using selected organisms on renewable substrates. Most biosurfactant-producing organisms produce biosurfactants in response to the presence of a hydrocarbon source (e.g., oils, sugar, glycerol, etc.) in the growing media. Other media components such as concentration of iron can also affect biosurfactant production significantly. For example, the production of RLP by *Pseudomonas* spp. can be increased if nitrate is used as a source of nitrogen rather than ammonium. Also the concentration of iron, magnesium, sodium, and potassium; the carbon:phosphorus ratio; and agitation can greatly affect rhamnolipid production.

All biosurfactants are amphiphiles. They consist of two parts: a polar (hydrophilic) moiety and non-polar (hydrophobic) group. Due to their amphiphilic structure, biosurfactants increase the surface area of hydrophobic water-insoluble substances, increase the water bioavailability of such substances, and change the properties of bacterial cell surfaces.

Biosurfactants include low molecular weight glycolipids (e.g., rhamnolipids, sophorolipids, mannosylerythritol lipids), lipopeptides (e.g., surfactin), flavolipids, phospholipids, and high molecular weight polymers such as lipoproteins, lipopolysaccharide-protein complexes, and polysaccharide-protein-fatty acid complexes. The common lipophilic moiety of a biosurfactant molecule is the hydrocarbon chain of a fatty acid, whereas the hydrophilic part is formed by ester or alcohol groups of neutral lipids, by the carboxylate group of fatty acids or amino acids (or peptides), organic acid in the case of flavolipids, or, in the case of glycolipids, by the carbohydrate.

Microbial biosurfactants are produced by a variety of microorganisms such as bacteria, fungi, and yeasts. Exemplary biosurfactant-producing microorganisms include *Starmerella* spp. (*S. bombicola*), *Pseudomonas* spp. (*P. aeruginosa, P. putida, P. florescens, P. Tragi, P. syringae*); *Flavobacterium* spp.; *Bacillus* spp. (*B. subtilis, B. pumillus, B. cereus, B. licheniformis*); *Wickerhamomyces* spp., *Candida* spp. (*C. albicans, C. rugosa, C. tropicalis, C. lipolytica, C. torulopsis*); *Rhodococcus* spp.; *Arthrobacter* spp.; *Campylobacter* spp.; *Cornybacterium* spp.; *Pichia* spp.; *Starmerella* spp.; as well as others listed herein.

In one embodiment of the subject invention, the biosurfactants produced by the subject systems include surfactin and glycolipids such as rhamnolipids (RLP), sophorolipids (SLP), trehalose lipids or mannosylerythritol lipids (MEL). In particular embodiments, the subject system is used to produce SLPs and/or MELs on a large scale.

Sophorolipids are glycolipid biosurfactants produced by, for example, various yeasts of the *Starmerella* clade. Among yeasts of the *Starmerella* clade that have been examined, the greatest yield of sophorolipids has been reported from *Candida apicola* and *Starmerella bombicola*. SLPs consist of a disaccharide sophorose linked to long chain hydroxy fatty acids. These SLPs are a partially acetylated 2-O-β-D-glucopyranosyl-D-glucopyranose unit attached β-glycosidically to 17-L-hydroxyoctadecanoic or 17-L-hydroxy-Δ9-octadecenoic acid. The hydroxy fatty acid is generally 16 or 18 carbon atoms, and may contain one or more unsaturated bonds. The fatty acid carboxyl group can be free (acidic or open form) or internally esterified at the 4"-position (lactone form).

Mannosylerythritol lipids are a glycolipid class of biosurfactants produced by a variety of yeast and fungal strains. Effective MEL production is limited primarily to the genus *Pseudozyma*, with significant variability among the MEL structures produced by each species. MELs contain 4-O-b-D-mannopyranosyl-erythritol as their sugar moiety or a hydrophilic unit. According to the degree of acetylation at C-4' and C-6' positions in mannopyranosyl, MELs are classified as MEL-A, MEL-B, MEL-C and MEL-D. MEL-A represents the diacetylated compound whereas MEL-B and MEL-C are monoacetylated at C-6' and C-4', respectively. The completely deacetylated structure is attributed to MEL-D. Outside of *Pseudozyma*, a recently isolated strain, *Ustilago scitaminea*, has been shown to exhibit abundant MEL-B production from sugarcane juice. MELs act as effective topical moisturizers and can repair damaged hair. Furthermore, these compounds have been shown to exhibit both protective and healing activities, to activate fibroblasts and papilla cells, and to act as natural antioxidants.

Due to the structure and composition of SLPs and MELs, these biosurfactants have excellent surface and interfacial tension reduction properties, as well as other beneficial biochemical properties, which can be useful in applications such as large scale industrial and agriculture uses, and in other fields, including but not limited to cosmetics, household products, and health, medical and pharmaceutical fields.

Biosurfactants accumulate at interfaces, thus reducing interfacial tension and leading to the formation of aggregated micellular structures in solution. Safe, effective microbial biosurfactants reduce the surface and interfacial tensions between the molecules of liquids, solids, and gases. The ability of biosurfactants to form pores and destabilize biological membranes permits their use as antibacterial, antifungal, and hemolytic agents. Combined with the characteristics of low toxicity and biodegradability, biosurfactants are advantageous for use in the oil and gas industry for a wide variety of petroleum industry applications, such as microbially enhanced oil recovery. These applications include, but are not limited to, enhancement of crude oil recovery from an oil-containing formation; stimulation of oil and gas wells (to improve the flow of oil into the well bore); removal of contaminants and/or obstructions such as paraffins, asphaltenes and scale from equipment such as rods, tubing, liners, tanks and pumps; prevention of the corrosion of oil and gas production and transportation equipment; reduction of $H_2S$ concentration in crude oil and natural gas; reduction in viscosity of crude oil; upgradation of heavy crude oils and asphaltenes into lighter hydrocarbon fractions; cleaning of tanks, flowlines and pipelines; enhancing the mobility of oil during water flooding though selective and non-selective plugging; and fracturing fluids.

When used in oil and gas applications, the systems of the present invention can be used to lower the cost of microbial-based oilfield compositions and can be used in combination with other chemical enhancers, such as polymers, solvents, fracking sand and beads, emulsifiers, surfactants, and other materials known in the art.

Biosurfactants produced according to the subject invention can be used for other, non-oil recovery purposes including, for example, cleaning pipes, reactors, and other machinery or surfaces, as well as pest control, for example, when applied to plants and/or their surrounding environment. Some biosurfactants produced according to the subject invention can be used to control pests because they are able to penetrate through pests' tissues and are effective in low amounts without the use of adjuvants. It has been found that at concentrations above the critical micelle concentration, the biosurfactants are able to penetrate more effectively into treated objects.

Pests can be controlled using either the biosurfactant-producing organisms as a biocontrol agent or by the biosurfactants themselves. In addition, pest control can be achieved by the use of specific substrates to support the growth of biosurfactant-producing organisms as well as to produce biosurfactant pesticidal agents. Advantageously, natural biosurfactants are able to inhibit the growth of competing organisms and enhance the growth of the specific biosurfactant-producing organisms.

In addition, these biosurfactants can play important roles in treating animal and human diseases. Animals can be treated by, for example, by dipping or bathing in a biosurfactant solution alone, with or without microbe cell mass, and/or in the presence of other compounds such as copper or zinc.

The compositions produced according to the present invention have advantages over biosurfactants alone due to the use of entire cell culture, including: high concentrations of mannoprotein as a part of yeast cell wall's outer surface (mannoprotein is a highly effective bioemulsifier capable of reaching up to an 80% emulsification index); the presence of the biopolymer beta-glucan (an emulsifier) in yeast cell walls; and the presence of biosurfactants and other metabolites (e.g., lactic acid, ethanol, etc.) in the culture. These compositions can, among many other uses, can have surface/interfacial tension-reducing properties.

Methods of Cultivation Using the Subject Reactor Systems

Referring to FIGS. 1-4, In one embodiment, the subject invention provides methods of cultivating microorganisms using the subject reactor system 10. Advantageously, in one embodiment, the methods can be performed without contamination.

In one embodiment, the subject invention provides methods of cultivating microorganisms without contamination using the subject reactor system. In certain embodiments, the methods of cultivation comprise adding a culture medium comprising water and nutrient components to the tank 100; inoculating the reactor system 10 with a viable microorganism; and optionally, adding an antimicrobial agent to the culture medium. The antimicrobial agent can be, for example, an antibiotic (when permissible based on e.g., location of use or product being produced) or a glycolipid (e.g., sophorolipids, rhamnolipids).

Advantageously, the method and equipment of the subject invention reduce the capital and labor costs of producing microorganisms and their metabolites on a large scale. Furthermore, the cultivation process of the subject invention reduces or eliminates the need to concentrate organisms after completing cultivation. The subject invention provides a cultivation method that not only substantially increases the yield of microbial products per unit of nutrient medium but simplifies production and facilitates portability.

Portability can result in significant cost savings as microbe-based compositions can be produced at, or near, the site of intended use. This means that the final composition can be manufactured on-site using locally-sourced materials if desired, thereby reducing shipping costs. Thus, the compositions can include viable microbes at the time of application, which can increase product effectiveness. Additionally, the compositions can be customized in real time to be ideal for conditions at a particular location.

Furthermore, in certain embodiments, the systems 10 of the subject invention harness the power of naturally-occurring local microorganisms and their metabolic by-products. Use of local microbial populations can be advantageous in settings including, but not limited to, agriculture, environmental remediation (such as in the case of an oil spill), animal husbandry, aquaculture, forestry, pasture management, turf management, horticultural ornamental production, waste disposal and treatment, wastewater treatment, food production and procession, mining, oil recovery, and human health, including in remote locations.

The subject invention provides methods and systems for the efficient production of microbes using novel biological reactors 10. The system can include all of the materials necessary for the fermentation (or cultivation) process, including, for example, equipment, sterilization supplies, and culture medium components, although it is expected that freshwater could be supplied from a local source and sterilized according to the subject methods.

In one embodiment, the reactor system 10 is provided with an inoculum of viable microbes. Preferably, the microbes are biochemical-producing microbes, capable of accumulating, for example, biosurfactants, enzymes, solvents, biopolymers, acids, and/or other useful metabolites. In particularly preferred embodiments, the microorganisms are biochemical-producing yeast (including killer yeasts), fungi, and/or bacteria, including without limitation those listed herein.

In one embodiment, the reactor system 10 is provided with a culture medium. The medium can include nutrient sources, for example, a carbon source, a lipid source, a nitrogen source, and/or a micronutrient source. Each of the carbon source, lipid source, nitrogen source, and/or micronutrient source can be provided in an individual package that can be added to the reactor at appropriate times during the fermentation process. Each of the packages can include several sub-packages that can be added at specific points (e.g., when yeast, pH, and/or nutrient levels go above or below a specific concentration) or times (e.g., after 10 hours, 20 hours, 30 hours, 40 hours, etc.) during the fermentation process.

In one embodiment, fermentation medium, air, and equipment used in the cultivation process are sterilized. The cultivation equipment, such as the tank 100, may be separated from, but connected to, a sterilizing unit, e.g., an autoclave or a steamer (not shown).

In a specific embodiment, the method of cultivation comprises sterilizing the subject reactor system 10 prior to fermentation. The cultivation equipment may have a sterilizing unit that sterilizes in situ before starting the inoculation, e.g., by using a steamer (not shown).

In some embodiments, before fermentation, the reactor system 10 can be washed with a hydrogen peroxide solution (e.g., from 2.0% to 4.0% hydrogen peroxide; this can be done before or after a hot water rinse at, e.g., 80-90° C.) to prevent contamination. In addition, or in the alternative, the tank 100 can be washed with a commercial disinfectant, a bleach solution and/or a hot water or steam rinse.

The reactor system 100 can come with concentrated forms of the bleach and hydrogen peroxide, which can later be diluted at the fermentation site before use. For example, the hydrogen peroxide can be provided in concentrated form and be diluted to formulate 2.0% to 4.0% hydrogen peroxide (by weight or volume) for pre-rinse decontamination.

The internal surfaces of the reactor (including, e.g., tanks, ports, spargers and mixing systems) can first be washed with a commercial disinfectant; then fogged (or sprayed with a highly dispersed spray system) with 2% to 4% hydrogen peroxide, preferably 3% hydrogen peroxide; and finally steamed at a temperature of about 105° C. to about 110° C., or greater.

The air can be sterilized by methods know in the art. For example, air can pass through at least one filter 131 before being supplemented into the tank 100.

The culture medium components (e.g., the carbon source, water, lipid source, micronutrients, etc.) can also be sterilized. This can be achieved using temperature decontamination (e.g., autoclaving) and/or hydrogen peroxide decontamination (potentially followed by neutralizing the hydrogen peroxide using an acid such as HCl, $H_2SO_4$, etc.).

In some embodiments, the culture medium is sterilized inside the reactor system. After adding the medium to the tank 100, the temperature inside the tank is increased to boiling by circulating the medium through the external circulation system. The medium is then boiled for an amount of time to control undesirable contaminating organisms, and the system 10 is allowed to return to a lower temperature suitable for inoculating the system 10 with a viable microorganism.

In other embodiments, the medium may be pasteurized or optionally no heat at all added, where the use of low water activity and low pH may be exploited to control unwanted bacterial growth.

In a specific embodiment, the water used in the culture medium is UV sterilized using an in-line UV water sterilizer (not shown) and filtered using, for example, a sub-micron water filter and/or a carbon filter (not shown).

To further prevent contamination, the culture medium of the system may comprise additional acids, antibiotics, and/or antimicrobials, added before, and/or during the cultivation process. The one or more antimicrobial substances can include, e.g., streptomycin, oxytetracycline, sophorolipids, and rhamnolipids. The addition of antibiotics will depend upon local regulations and/or other factors that may prohibit their use.

Inoculation can take place in the tank 100, at which point the inoculum is mixed using the chaotic mixing scheme 110 and 120. Total fermentation times can range from 10 to 200 hours, preferably from 20 to 180 hours.

The fermenting temperature utilized in the subject systems 10 and methods can be, for example, from about 25 to 40° C., although the process may operate outside of this range. In one embodiment, the method for cultivation of microorganisms is carried out at about 5° to about 100° C., preferably, 15° to 60° C., more preferably, 25 to 50° C. In a further embodiment, the cultivation may be carried out continuously at a constant temperature. In another embodiment, the cultivation may be subject to changing temperatures.

The pH of the medium should be suitable for the microorganism of interest. Buffering salts, and pH regulators, such as carbonates and phosphates, may be used to stabilize pH near an optimum value. When metal ions are present in high concentrations, use of a chelating agent in the liquid medium may be necessary.

In certain embodiments, the microorganisms can be fermented in a pH range from about 2.0 to about 10.0 and, more specifically, at a pH range of from about 3.0 to about 7.0 (by manually or automatically adjusting pH using bases, acids, and buffers; e.g., HCl, KOH, NaOH, $H_2SO_4$, and/or $H_3PO_4$). The invention can also be practiced outside of this pH range.

The fermentation can start at a first pH (e.g., a pH of 4.0 to 4.5) and later change to a second pH (e.g., a pH of 3.2-3.5) for the remainder of the process to help avoid contamination as well as to produce other desirable results (the first pH can be either higher or lower than the second pH).

In one embodiment, pH is adjusted from a first pH to a second pH after a desired accumulation of biomass is achieved, for example, from 0 hours to 200 hours after the start of fermentation, more specifically from 12 to 120 hours after, more specifically from 24 to 72 hours after.

In one embodiment, the moisture level of the culture medium should be suitable for the microorganism of interest. In a further embodiment, the moisture level may range from 20% to 90%, preferably, from 30 to 80%, more preferably, from 40 to 60%.

The cultivation processes of the subject invention can be anaerobic, aerobic, or a combination thereof. Preferably, the process is aerobic, keeping the dissolved oxygen concentration above 10 or 15% of saturation during fermentation, but within 20% in some embodiments, or within 30% in some embodiments.

Advantageously, the system 10 provides easy oxygenation of the growing culture with, for example, the sparging system 140 in combination with the chaotic mixing scheme 110 and 120. Constant circulation of culture and injection of microbubbles from the sparging system 140 allows the system 10 to introduce and circulate oxygenated air. The oxygenated air may be ambient and/or filtered air supplemented continuously or periodically, such as daily.

In one embodiment, the culture medium used in the subject system 10, may contain supplemental nutrients for the microorganism. Typically, these include carbon sources, proteins, fats, or lipids, nitrogen sources, trace elements, and/or growth factors (e.g., vitamins, pH regulators). It will be apparent to one of skill in the art that nutrient concentration, moisture content, pH, and the like may be modulated to optimize growth for a particular microbe.

The lipid source can include oils or fats of plant or animal origin which contain free fatty acids or their salts or their esters, including triglycerides. Examples of fatty acids include, but are not limited to, free and esterified fatty acids containing from 16 to 18 carbon atoms, hydrophobic carbon sources, palm oil, animal fats, coconut oil, oleic acid, soybean oil, sunflower oil, canola oil, stearic and palmitic acid.

The culture medium of the subject system 10 can further comprise a carbon source. The carbon source is typically a carbohydrate, such as glucose, xylose, sucrose, lactose, fructose, trehalose, galactose, mannose, mannitol, sorbose, ribose, and maltose; organic acids such as acetic acid, fumaric acid, citric acid, propionic acid, malic acid, malonic acid, and pyruvic acid; alcohols such as ethanol, propanol, butanol, pentanol, hexanol, erythritol, isobutanol, xylitol, and glycerol; fats and oils such as canola oil, soybean oil, rice bran oil, olive oil, corn oil, sesame oil, and linseed oil; etc. Other carbon sources can include arbutin, raffinose, gluconate, citrate, molasses, hydrolyzed starch, potato extract, corn syrup, and hydrolyzed cellulosic material. The above carbon sources may be used independently or in a combination of two or more.

In one embodiment, growth factors and trace nutrients for microorganisms are included in the medium of the system 10. This is particularly preferred when growing microbes that are incapable of producing all of the vitamins they require. Inorganic nutrients, including trace elements such as iron, zinc, potassium, calcium copper, manganese, molybdenum and cobalt; phosphorous, such as from phosphates; and other growth stimulating components can be included in the culture medium of the subject systems. Furthermore, sources of vitamins, essential amino acids, and microelements can be included, for example, in the form of flours or meals, such as corn flour, or in the form of extracts, such as yeast extract, potato extract, beef extract, soybean extract, banana peel extract, and the like, or in purified forms. Amino acids such as, for example, those useful for biosynthesis of proteins, can also be included.

In one embodiment, inorganic or mineral salts may also be included. Inorganic salts can be, for example, potassium dihydrogen phosphate, dipotassium hydrogen phosphate, disodium hydrogen phosphate, magnesium sulfate, magnesium chloride, iron sulfate, iron chloride, manganese sulfate, manganese chloride, zinc sulfate, lead chloride, copper sulfate, calcium chloride, calcium carbonate, sodium carbonate. These inorganic salts may be used independently or in a combination of two or more.

The culture medium of the subject system 10 can further comprise a nitrogen source. The nitrogen source can be, for example, in an inorganic form such as potassium nitrate, ammonium nitrate, ammonium sulfate, ammonium phosphate, ammonia, urea, and ammonium chloride, or an organic form such as proteins, amino acids, yeast extracts, yeast autolysates, corn peptone, casein hydrolysate, and soybean protein. These nitrogen sources may be used independently or in a combination of two or more.

The microbes can be grown in planktonic form or as biofilm. In the case of biofilm, the tank 100 may have within it a substrate (not shown) upon which the microbes can be grown in a biofilm state. The system 10 may also have, for example, the capacity to apply stimuli (such as shear stress) that encourages and/or improves the biofilm growth characteristics.

In one embodiment, the subject invention further provides a composition comprising at least one type of microorganism and/or at least one microbial growth by-product produced by said microorganism. The microorganisms in the final composition may be in an active or inactive form and/or in the form of vegetative cells, spores, mycelia, conidia and/or any form of microbial propagule. The final composition may or may not comprise the medium in which the microbes were grown. The final composition may also be in a dried form or a liquid form.

In one embodiment, the microbe-based composition does not need to be further processed after fermentation (e.g., yeast, metabolites, and remaining carbon sources do not need to be separated from the sophorolipids). The physical properties of the final product (e.g., viscosity, density, etc.) can also be adjusted using various chemicals and materials that are known in the art.

In one embodiment, the microbe-based composition comprises a microbial metabolite but not the microorganism, where the microorganism(s) are separated from the metabolite(s) and/or other culture medium components. The method for producing microbial growth by-products may further comprise steps of extracting, concentrating and/or purifying the by-product of interest.

In one embodiment, the subject invention further provides customizations to the materials and methods according to the local needs. For example, the method for cultivation of microorganisms may be used to grow those microorganisms located in the local soil or at a specific oil well or site of pollution. Advantageously, in some embodiments, these microorganisms can be beneficial and more adaptable to local needs.

The cultivation method according to the subject invention not only substantially increases the yield of microbial products per unit of nutrient medium but also improves the simplicity of the production operation. Furthermore, the cultivation process can eliminate or reduce the need to concentrate microorganisms after finalizing fermentation.

Advantageously, the method does not require complicated equipment or high energy consumption, and thus reduces the capital and labor costs of producing microorganisms and their metabolites on a large scale.

Preparation of Microbe-Based Products

The subject invention can be utilized to produce useful microbe-based products, which can include products comprising the microbes and/or microbial growth by-products and optionally, the growth medium and/or additional ingredients such as, for example, water, carriers, adjuvants, nutrients, viscosity modifiers, and other active agents.

One microbe-based product of the subject invention is simply the fermentation medium containing the microorganism and/or the microbial growth by-products produced by the microorganism and/or any residual nutrients. The product of fermentation may be used directly without extraction or purification. If desired, extraction and purification can be easily achieved using standard extraction methods or techniques known to those skilled in the art.

The microorganisms in the microbe-based products may be in an active or inactive form and/or in the form of vegetative cells, spores, mycelia, conidia and/or any form of microbial propagule. The microbe-based products may be used without further stabilization, preservation, and storage. Advantageously, direct usage of these microbe-based products preserves a high viability of the microorganisms, reduces the possibility of contamination from foreign agents and undesirable microorganisms, and maintains the activity of the by-products of microbial growth.

Referring to FIGS. 1-4, the microbes and/or medium resulting from the microbial growth can be removed from the reactor system 10 and transferred via, for example, piping for immediate use.

In other embodiments, the composition (microbes, medium, or microbes and medium) can be placed in containers (not shown) of appropriate size, taking into consideration, for example, the intended use, the contemplated method of application, the size of the fermentation tank 100, and any mode of transportation from microbe growth facility to the location of use. Thus, the containers into which the microbe-based composition is placed may be, for example, from 1 gallon to 1,000 gallons or more. In other embodiments the containers are 2 gallons, 5 gallons, 25 gallons, or larger. The microbe-based compositions can be combined with other microbe-based compositions in one container.

Upon harvesting the microbe-based composition from the reactor systems 10, further components can be added as the harvested product is placed into containers and/or piped (or otherwise transported for use). The additives can be, for example, buffers, carriers, other microbe-based compositions produced at the same or different facility, viscosity modifiers, preservatives, nutrients for microbe growth, nutrients for plant growth, tracking agents, pesticides, herbicides, animal feed, food products and other ingredients specific for an intended use.

Advantageously, in accordance with the subject invention, the microbe-based product may comprise broth in which the microbes were grown. The product may be, for example, at least, by weight, 1%, 5%, 10%, 25%, 50%, 75%, or 100% broth. The amount of biomass in the product, by weight, may be, for example, anywhere from 0% to 100% inclusive of all percentages therebetween.

Optionally, the product can be stored prior to use. The storage time is preferably short. Thus, the storage time may be less than 60 days, 45 days, 30 days, 20 days, 15 days, 10 days, 7 days, 5 days, 3 days, 2 days, 1 day, or 12 hours. In a preferred embodiment, if live cells are present in the product, the product is stored at a cool temperature such as, for example, less than 20° C., 15° C., 10° C., or 5° C. On the other hand, a biosurfactant composition can typically be stored at ambient temperatures.

The subject invention provides microbe-based products, as well as uses for these products to achieve beneficial results in many settings including, for example, improved bioremediation, mining, and oil and gas production; food production and processing; waste disposal and treatment; enhanced health of livestock and other animals; and enhanced health and productivity of plants, by applying one or more of the microbe-based products to a desired site. The microbe-based products can serve as, for example, microbial inoculants, biopesticides, nutrient sources, remediation agents, cosmetic and/or health products, cleaning agents, and/or biosurfactants. In one embodiment, the fermentation products (e.g., microorganisms and/or metabolites) obtained after the cultivation process are typically of high commercial value.

The microorganisms may be present in the composition as the cultivation broth and/or as cultivation biomass. The cultivation broth and/or biomass may be dried (e.g., spray-dried), to produce the products of interest. The biomass may be separated by known methods, such as centrifugation, filtration, separation, decanting, a combination of separation and decanting, ultrafiltration or microfiltration.

In one embodiment, the cultivation products may be used as an animal feed or as food supplement for humans. In one embodiment, the cultivation products have a high nutritional content. As a result, a higher percentage of the cultivation products may be used in, for example, a complete animal feed. In one embodiment, the feed composition comprises the modified cultivation products ranging from 15% of the feed to 100% of the feed.

The cultivation products may be rich in at least one or more of fats, fatty acids, lipids such as phospholipid, vitamins, essential amino acids, peptides, proteins, carbohydrates, sterols, enzymes, and trace minerals such as, iron, copper, zinc, manganese, cobalt, iodine, selenium, molybdenum, nickel, fluorine, vanadium, tin and silicon. The peptides may contain at least one essential amino acid.

In one embodiment, the essential amino acids are encapsulated inside a modified microorganism. The essential amino acids are contained in heterologous polypeptides expressed by the microorganism. Where desired, the heterologous peptides are expressed and stored in the inclusion bodies in a suitable microorganism (e.g., fungi).

The microbes and microbial growth by-products of the subject invention can also be used for the transformation of a substrate, such as an ore, wherein the transformed substrate is the product.

In specific embodiments, the systems of the subject invention improve agricultural productivity by, for example, enabling local production of customized agricultural products for promoting crop vitality; enhancing crop yields; enhancing plant immune responses; enhancing insect, pest and disease resistance; controlling insects, nematodes, diseases and weeds; improving plant nutrition; improving the nutritional content of agricultural and forestry and pasture soils; and promoting improved and more efficient water use.

In one embodiment, the microbe-based products can be applied to soil, seeds, or plant parts to increase crop yield and/or plant health and growth. Advantageously, the microbe-based products can be used to effectively control nematodes and other pests, and the corresponding diseases caused by pests while a yield increase is achieved.

Compositions produced by the present invention can also be used in a wide variety of petroleum industry applications, such as microbially-enhanced oil recovery. These applications include, but are not limited to, enhancement of crude oil recovery; stimulation of oil and gas wells (to improve the flow of oil into the well bore); removal of contaminants and/or obstructions such as paraffins, asphaltenes and scale from equipment such as rods, tubing, liners, tanks and pumps; prevention of the corrosion of oil and gas production and transportation equipment; reduction of $H_2S$ concentration in crude oil and natural gas; reduction in viscosity of crude oil; upgradation of heavy crude oils and asphaltenes into lighter hydrocarbon fractions; cleaning of tanks, flow-lines and pipelines; enhancing the mobility of oil during water flooding though selective and non-selective plugging; drilling fluids and fracturing fluids.

When used by oil and gas producers, the systems of the present invention can be used to lower the cost of microbial-based oilfield compositions and can be used in combination with other chemical enhancers, such as polymers, solvents, enzymes, drilling fluids, condensates, fracking sand and beads, emulsifiers, surfactants, and other materials known in the art.

Local Production of Microbe-Based Products

In certain embodiments of the subject invention, a microbe growth facility produces fresh, high-density microorganisms and/or microbial growth by-products of interest on a desired scale. The microbe growth facility may be located at or near the site of application. Referring to FIGS. 1-4, The facility comprises one or a plurality of the reactor systems 10 of the subject invention to produce high-density microbe-based compositions in batch, quasi-continuous, or continuous cultivation.

The microbe growth facilities of the subject invention can be located at the location where the microbe-based product will be used (e.g., a citrus grove). For example, the microbe growth facility may be less than 300, 250, 200, 150, 100, 75, 50, 25, 15, 10, 5, 3, or 1 mile from the location of use.

Because the microbe-based product can be generated locally, without resort to the microorganism stabilization, preservation, storage and transportation processes of conventional microbial production, a much higher density of microorganisms can be generated, thereby requiring a smaller volume of the microbe-based product for use in the on-site application or which allows much higher density microbial applications where necessary to achieve the desired efficacy. Local generation of the microbe-based product also eliminates the need for cell stabilization and facilitates the inclusion of the growth medium in the product. The medium can contain agents produced during the fermentation that are particularly well-suited for local use.

Locally-produced high density, robust cultures of microbes are more effective in the field than those that have remained in the supply chain for some time. The microbe-based products of the subject invention are particularly advantageous compared to traditional products wherein cells have been separated from metabolites and nutrients present in the fermentation growth media. Reduced transportation times allow for the production and delivery of fresh batches of microbes and/or their metabolites at the time and volume as required by local demand.

The microbe growth facilities of the subject invention produce fresh, microbe-based compositions, comprising the microbes themselves, microbial metabolites, and/or other components of the medium in which the microbes are grown. If desired, the compositions can have a high density of vegetative cells or propagules, or a mixture of vegetative cells and propagules.

In one embodiment, the microbe growth facility is located on, or near, a site where the microbe-based products will be used (e.g., a citrus grove), for example, within 300 miles, 200 miles, or even within 100 miles. Advantageously, this allows for the compositions to be tailored for use at a specified location. The formula and potency of microbe-based compositions can be customized for specific local conditions at the time of application, such as, for example, which soil type, plant and/or crop is being treated; what season, climate and/or time of year it is when a composition is being applied; and what mode and/or rate of application is being utilized.

Advantageously, distributed microbe growth facilities provide a solution to the current problem of relying on far-flung industrial-sized producers whose product quality suffers due to upstream processing delays, supply chain bottlenecks, improper storage, and other contingencies that inhibit the timely delivery and application of, for example, a viable, high cell-count product and the associated medium and metabolites in which the cells are originally grown.

Furthermore, by producing a composition locally, the formulation and potency can be adjusted in real time to a specific location and the conditions present at the time of application. This provides advantages over compositions that are pre-made in a central location and have, for example, set ratios and formulations that may not be optimal for a given location.

The microbe growth facilities provide manufacturing versatility by their ability to tailor the microbe-based products to improve synergies with destination geographies. Advantageously, in preferred embodiments, the systems of the subject invention harness the power of naturally-occurring local microorganisms and their metabolic by-products.

The cultivation time for the individual reactor systems 10 may be, for example, from 1 to 7 days or longer. The cultivation product can be harvested in any of a number of different ways.

Local production and delivery within, for example, 24 hours of fermentation results in pure, high cell density compositions and substantially lower shipping costs. Given the prospects for rapid advancement in the development of more effective and powerful microbial inoculants, consumers will benefit greatly from this ability to rapidly deliver microbe-based products.

Cultivation of microbial biosurfactants according to the prior art is a complex, time and resource consuming, process that requires multiple stages. The subject invention provides equipment, apparatuses, methods and systems that simplify and reduce the cost of this process. The subject invention also provides novel compositions and uses of these compositions.

EXAMPLES

A greater understanding of the present invention and of its many advantages may be had from the following examples, given by way of illustration. The following examples are illustrative of some of the methods, applications, embodiments and variants of the present invention. They are not to be considered as limiting the invention. Numerous changes and modifications can be made with respect to the invention.

Example 1—Stainless Steel "Cube" Fermentation Reactor System

Referring to FIGS. 1-4, the "Cube" comprises a 550 gallon stainless steel tank 100. The unit 10 is 5×5 feet, and about 6 feet tall. The unit 10 comes equipped with a PLC 170 connected to probes 150 that monitor temperature, DO and pH level throughout fermentation. The unit 10 is also equipped with an automated steam sterilization cycle (not shown).

The unit 10 has an internal mixing system 110 comprising a 2 horsepower sanitary sealed mixing motor 111. The mixing motor 111 is rotatably attached to a metal shaft 112 having an impeller 113 thereon. The impeller 113 comprises a 22-inch axial flow aeration turbine and/or a small 8-inch marine prop to help propel tank liquid from the top of the tank to the bottom. The shaft 112 and impeller 113 rotate on a diagonal axis (e.g., an axis at 15 to 60° from vertical) to enhance mixing.

Temperature control does not use a jacket, but instead uses an external circulation system 120 comprising two 1-2 horsepower circulation pumps 123a, 123b that run tank liquid through two highly efficient external loops 120a, 120b with inline 250-400K heat exchangers 122a, 122b.

The pumps 123a, 123b pump chilled or heated liquid around the passing culture to maintain a set temperature in the reactor system 10. The two circulation pumps 123a, 123b transport liquid from the bottom of the tank 100 at 250 to 400 gallons per minute, through the heat exchangers 122a, 122b, and then back into the top of the tank 100. The heat exchangers 122a, 122b are attached to city water, and optionally, a chiller, which flows at a rate of about 13 gallons per minute around the culture.

The unit 10 comprises an aeration system 130 capable of providing 1 to 5 liters of filtered air per liter of culture per minute, or approximately 50-100 CFM, or 20 to 60 CFM of air, at a pressure of 30-80 PSI, to the culture. In some embodiments, the unit 10 requires 1 L/L of inlet air, which is about 40 CFM.

The unit 10 is also equipped with a sparging system 140 through which the aeration system 130 supplies the culture with air. The sparging system 140 comprises 4 custom-made, 2-micron sintered stainless steel aerators 141.

Example 2—Operation

A portable and distributable stainless steel reactor as described in Example 1 is used to produce microbe-based products. The reactor system is first sterilized using a three-step method.

Referring to FIGS. 1-4, The internal surfaces of the reactor system 10 (including, e.g., the tank 100, sparging system 140, internal mixing system 110, external circulation system 120) are washed using a commercial disinfectant. Then, the reactor system 10 is fogged with a 3% hydrogen peroxide solution. Finally, the inside of the reactor system 10 is subjected to steaming using a portable steamer at 105° C. to 110° C.

The culture medium nutrient components are decontaminated using an autoclave (not shown). The water used for the culture medium is UV sterilized using an in-line UV water sterilizer (not shown), and filtered through a 0.1-micron water filter 125. A peristaltic pump (not shown) is used to add the cultivation medium components to the reactor.

The fermentation temperature should generally be between about 22-28° C., depending on the microorganism and/or microbial growth by-product being cultivated.

The pH should be from about 2.0 to about 7.0, and preferably between about 3.0 to about 6.5, depending on the microorganism and/or microbial growth by-product being cultivated. Additionally, in order to further reduce the possibility of contamination, the cultivation process can begin at a first pH range and then be adjusted to a second pH range either higher or lower than the first pH range.

Under these cultivation conditions, industrially useful production of biomass, biosurfactants and other metabolites are achieved after as little as 24 hours and up to 20 days of fermentation. Upon completion of the fermentation, the culture can then be harvested from the reactor system 10 and applied for a variety of industrial purposes.

The reactor systems 10 can then be sterilized again and re-used for fermenting either the same microbe-based products or different microbe-based products. For example, the reactor systems 10 can be used to cultivate *Starmerella bombicola* for production of SLPs, sterilized according to the subject methods, and then used to produce SLPs again or to cultivate another microorganism, such as *Pseudozyma aphidis* for production of MELs.

Example 3—Use of "Cube" Fermentation System for Production of Sophorolipids

The subject systems can be used to produce sophorolipids (SLPs) on an industrial scale and without contamination of the production culture.

In one embodiment, the reactor system is inoculated with *Starmerella bombicola* yeast. The culture medium comprises a carbon source and a lipid, and is supplemented with up to 200 ppm pure sophorolipid.

The yeast and culture medium are incubated at pH 3.0-3.5 under aerobic conditions and for a period of time sufficient for initial accumulation of biomass (typically about 24 hours to about 48 hours). The temperature is held at 22° to 28° C. and dissolved oxygen concertation is held within 15% to 30% (of 100% ambient air). Once initial biomass accumulation is achieved, pH is adjusted to 5.5 and the process is continued.

When the culture acidifies to pH 3.5, the fermentation process continues, keeping the pH stable at this level until sufficient accumulation of SLP is achieved in the medium. The SLPs are then subsequently recovered from the fermentation medium for further processing and/or direct use.

Example 4—Use of "Cube" Fermentation System for Production of Mannosylerythritol Lipids A seed culture of *Pseudozyma aphidis* is produced at a pH of 6.2. The medium for cultivating the seed culture is comprised of (g/L):

Glucose, 50 g
$NH_4NO_3$, 0.5 g
$KH_2PO_4$, 0.5 g
$K_2HPO_4$, 0.5 g
$MgSO_4$, 0.2 g
Yeast Extract, 1 g The seed culture is cultivated for two days at 30° C. Referring to FIGS. 1-4, it is then used as an inoculant for producing MEL in the subject reactor system 10. The medium for MEL production at pH 6.2 comprises (g/L or mL/L):

$NaNO_3$, 2 g
$KH_2P4_3$, 0.2 g
$MgSO_4$, 0.2 g

Yeast Extract, 1 g
$H_2O$, 920 mL
Canola Oil, 80 mL (autoclaved separately).

The media volume is adjusted to the desired volume, minus the volume of canola oil. The medium can also be supplemented with up to 200 ppm pure sophorolipid.

The yeasts are incubated in the culture medium under aerobic conditions and for a period of time sufficient for initial accumulation of biomass (typically about 24 hours to about 48 hours). The temperature of cultivation is 27-30° C., DO at 5-30% (or from 15 to 20%), and air circulation at 1V/Vm. After two days of fermentation, 40 g/L erythritol in $H_2O$ is added. The fermentation process continues, keeping the pH stable until sufficient accumulation of MELs is achieved in the medium. Total fermentation time is 15 days.

Total MEL concentration that can be produced ranges from 50 to 100 g/L. The temperature can then be increased to 70-90° C. if inactivation of the yeast cells is desired. The oily layer (MELs) is then collected and can be prepared as a microbe-based product for a variety of uses, including the methods of the subject invention.

We claim:

1. A method for producing a yeast and/or a yeast metabolite, without contamination, the method comprising:
   adding a culture medium comprising water and a fatty acid source to a submerged fermentation system comprising a chaotic mixing scheme and a sparging system;
   inoculating the submerged fermentation system with a viable yeast to produce a culture;
   adding a sophorolipid or an antibiotic to the submerged fermentation system; and
   operating the submerged fermentation system for an amount of time to accumulate a desired cell concentration and/or a desired concentration of the yeast metabolite in the culture, wherein operating the submerged fermentation system comprises mixing the culture using the chaotic mixing scheme and aerating the culture with the sparging system,
   wherein the chaotic mixing scheme comprises an impeller and an external circulation system, and wherein the sparging system comprises multiple stainless steel microporous aerators, said stainless steel microporous aerators comprising a stainless steel pipe attached to an air supply, said stainless steel pipes comprising a plurality of holes 1 micron in diameter or less.

2. The method of claim 1, wherein the yeast is *Starmerella bombicola, Wickerhamomyces anomalus* or *Pseudozyma aphidis.*

3. The method of claim 1, wherein the yeast metabolite is a biosurfactant.

4. The method of claim 1, wherein the system of claim 1, wherein prior to inoculation, the culture medium is sterilized.

5. The method of claim 4, wherein the culture medium is sterilized by autoclave.

6. The method of claim 1, wherein the water of the culture medium is UV sterilized and/or filtered using a submicron filter.

7. The method of claim 1, wherein the culture medium comprises one or more carbohydrate sources, one or more lipid sources, one or more mineral salts, one or more micronutrient sources, and one or more nitrogen sources.

8. The method of claim 1, further comprising harvesting the yeast and/or the yeast metabolite from the system.

9. The method of claim 8, wherein the yeast metabolite is separated from the yeast and, optionally, concentrated and/or purified.

\* \* \* \* \*